(12) United States Patent
Tranchand-Bunel et al.

(10) Patent No.: US 6,818,219 B1
(45) Date of Patent: Nov. 16, 2004

(54) REAGENT FOR DETECTING AND MONITORING VIRAL INFECTIONS

(75) Inventors: Denis Tranchand-Bunel, Ronchin (FR); Hélène Gras-Masse, Merignies (FR); Claude Auriault, Nomain (FR); André Tartar, Vitry-en-Artois (FR); Eric Diesis, Haubourdin (FR); Brigitte Bourez, Leers (FR)

(73) Assignees: Institut Pasteur de Lille, Lille (FR); Centre National de la Recherche Scientifique-CNRS, Paris (FR)

( * ) Notice: Subject to any disclaimer, the term of this patent is extended or adjusted under 35 U.S.C. 154(b) by 0 days.

(21) Appl. No.: 09/446,907

(22) PCT Filed: Jul. 3, 1998

(86) PCT No.: PCT/FR98/01432
§ 371 (c)(1),
(2), (4) Date: Apr. 10, 2000

(87) PCT Pub. No.: WO99/01767
PCT Pub. Date: Jan. 14, 1999

(30) Foreign Application Priority Data

Jul. 4, 1997 (FR) .............................................. 97 08537

(51) Int. Cl.[7] .............................................. A61K 39/12
(52) U.S. Cl. ................................. 424/186.1; 424/192.1; 424/204.1; 424/235.1; 435/5; 530/350; 530/403
(58) Field of Search ............................ 424/186.1, 192.1, 424/204.1, 235.1; 435/5; 530/403, 350

(56) References Cited

U.S. PATENT DOCUMENTS 5,827,646 A * 10/1998 Middeldorp et al. ............ 435/5

FOREIGN PATENT DOCUMENTS

| EP | 0 442 394 | 8/1991 |
| EP | 0 508 427 | 10/1992 |
| EP | 0 574 048 | 12/1993 |
| EP | 0 649 904 | 4/1995 |
| EP | 0 754 755 | 1/1997 |
| WO | 93 18054 | 9/1993 |
| WO | 96 00784 | 1/1996 |
| WO | 96 30547 | 10/1996 |

OTHER PUBLICATIONS

Van Grunsven W. M. J. et al., "Localization and diagnostic application of immunodominant domains of the BFRF3–encoded Epstein –Barr virus capsid protein", Journal of Infectious Diseases, 170 (1), 1994, pp. 13–19.

Hsu T–Y et al., "Use of Antigen Expressed in Bacteria for Detection of EBV–Specific Thymidine Kinase Antibodies in Sera from Patients with Nasopharyngeal Carcinoma" J. Med. Virol, 38 (3), 1992, pp. 214–219.

Auriault, C. et al., "Immunological properties of synthetic peptide constructs from HIV and the parasite Schistosoma mansoni: Expertise in an immunoprophylactic strategy." Joint Meeting of the American Academy of Allergy, Asthma and Immunology Society, San Francisco, California, USA, Feb. 21–26, 1997. Journal of Allergy and Clinical Immunology 9.

* cited by examiner

Primary Examiner—Laurie Scheiner
(74) Attorney, Agent, or Firm—Oblon, Spivak, McClelland, Maier & Neustadt, P.C.

(57) ABSTRACT

The invention concerns a reagent for diagnosing an infection caused by a virus, characterized in that it comprises essentially a mixture consisting of (1) an immunodominant fragment of a protein of said virus comprising not more than 60 aminoacids, preferably between 20 and 30 aminoacids and (2) a mixture (called mixotope) of convergent combining peptides, derived from said immunodominant fragment, which peptides are obtained by total or partial artificial degeneration of said immunodominant fragment by systematic or partial replacement of each aminoacid by another according to an appropriate substitution matrix. The invention concerns a reagent for detecting and monitoring infections caused by the Epstein-Barr virus of EBV, which is, in particular, the causal agent of infectious mononucleose and its applications for detecting an EBV infection at any stage of the infection (primo-infection, healthy carriers and induced tumors). Said diagnosis reagent comprises essentially a mixture consisting of (1) a C-terminal fragment of the protein VCAp18 SEQ ID n° 1 of the Epstein-Barr virus (EBV) comprising not more than 60 aminoacids, preferably between 20 and 30 aminoacids, and (2) a mixture of convergent combining peptides, derived from said C-terminal fragment.

18 Claims, 21 Drawing Sheets

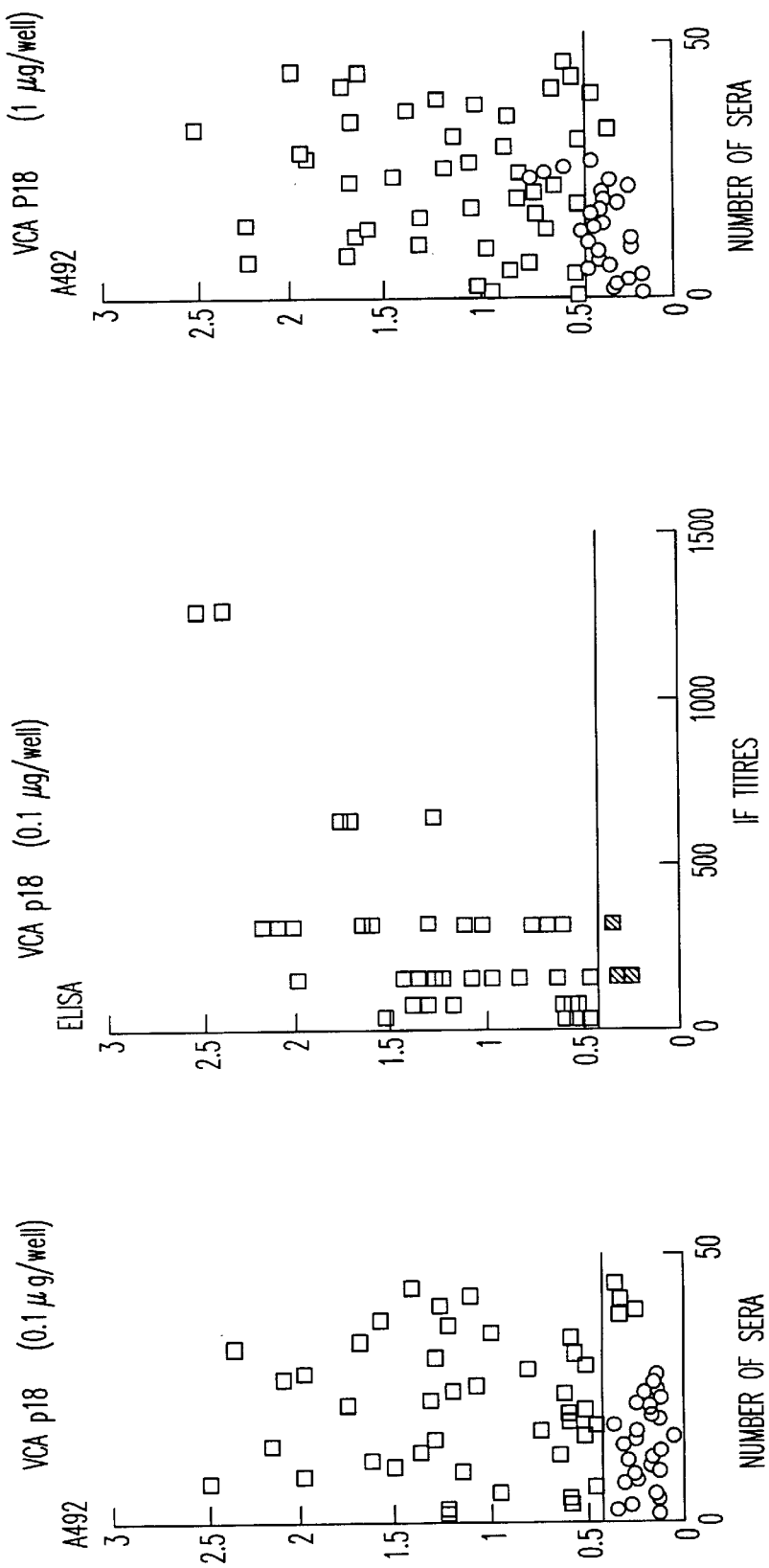

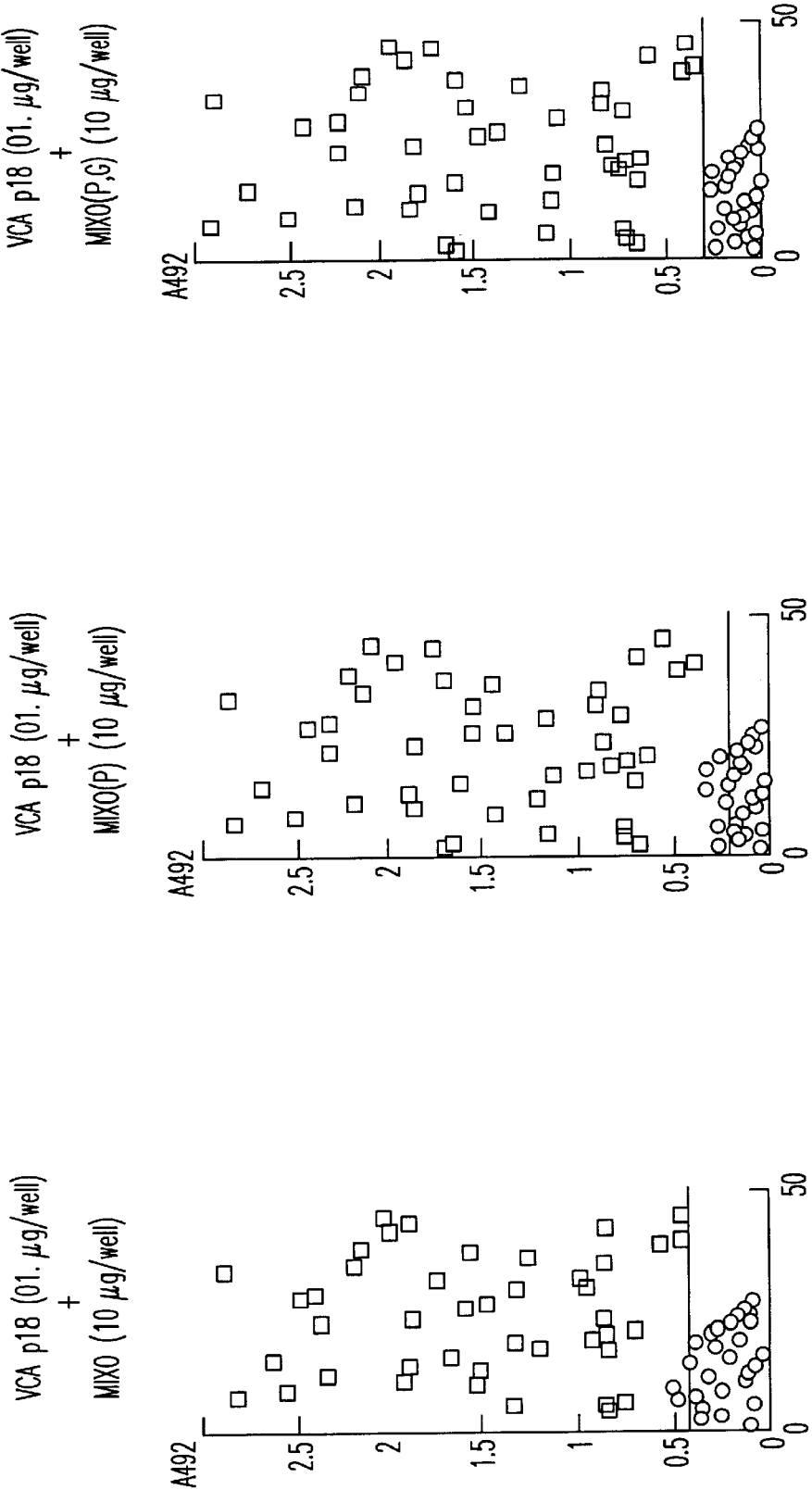

Serum 2986967

□ VCAp18
◇ MIXO
△ MIXO(P)
○ MIXO(P,G)

Serum 2987943

□ VCAp18
◇ MIXO
△ MIXO(P)
○ MIXO(P,G)

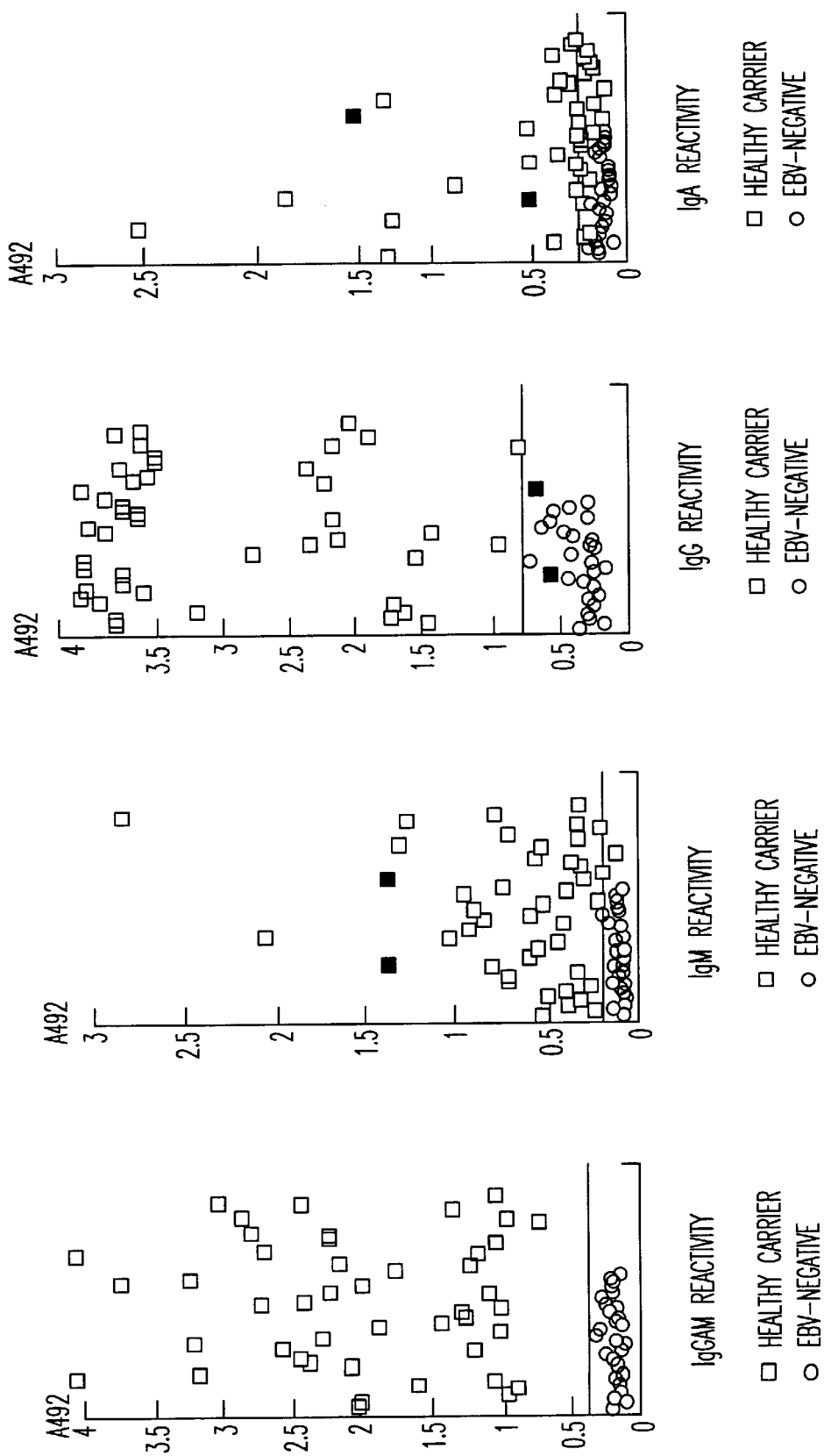

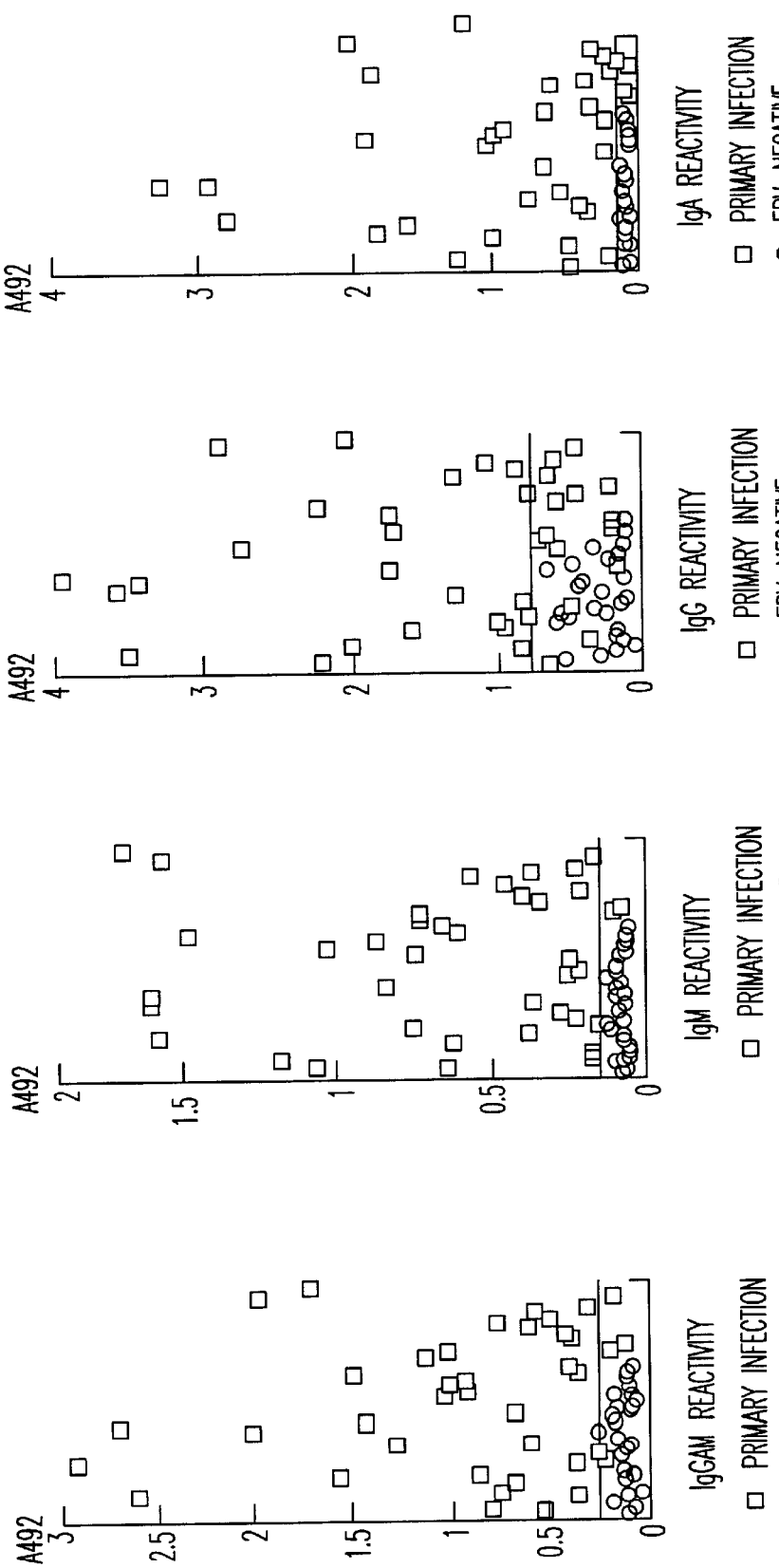

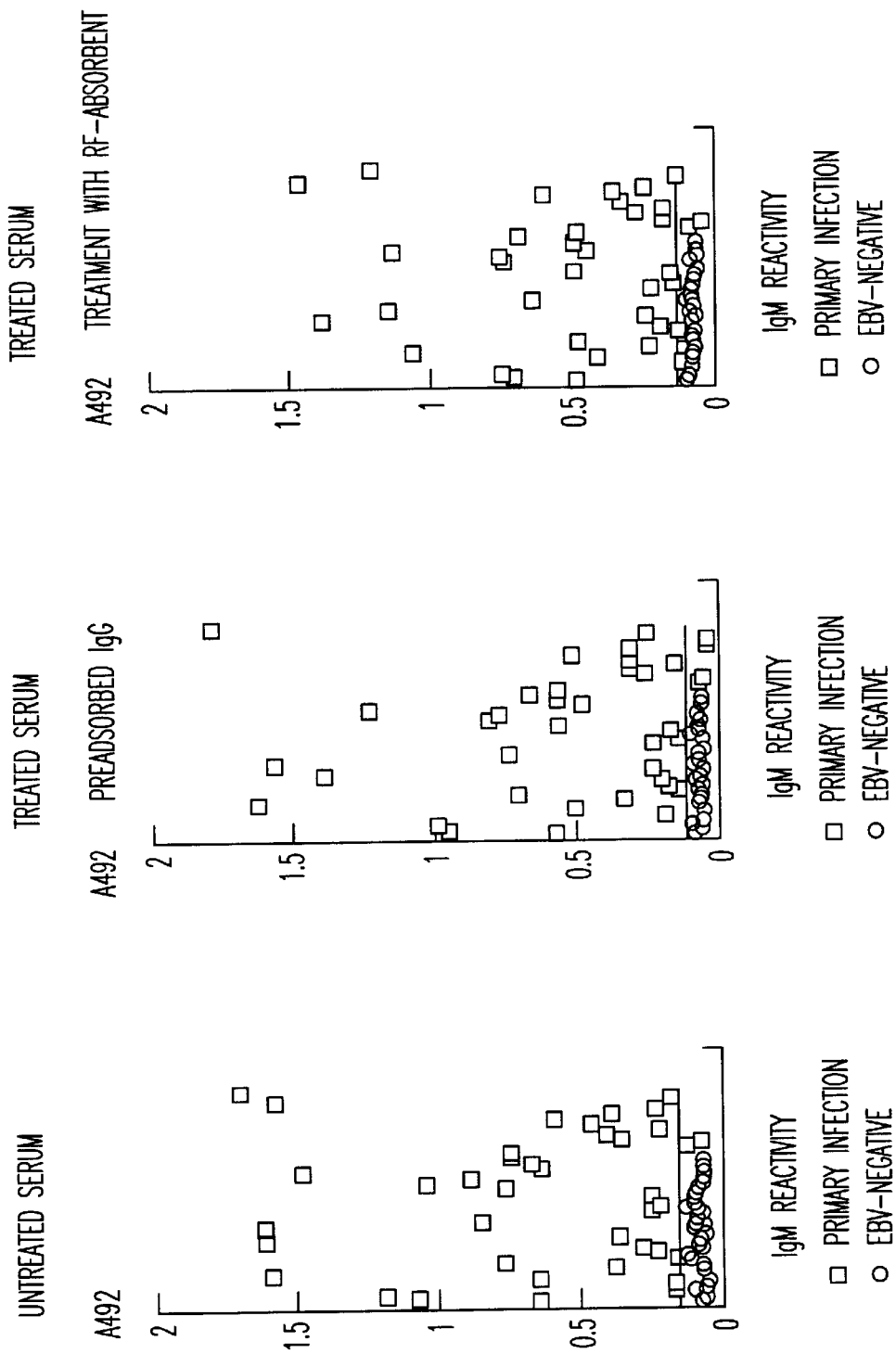

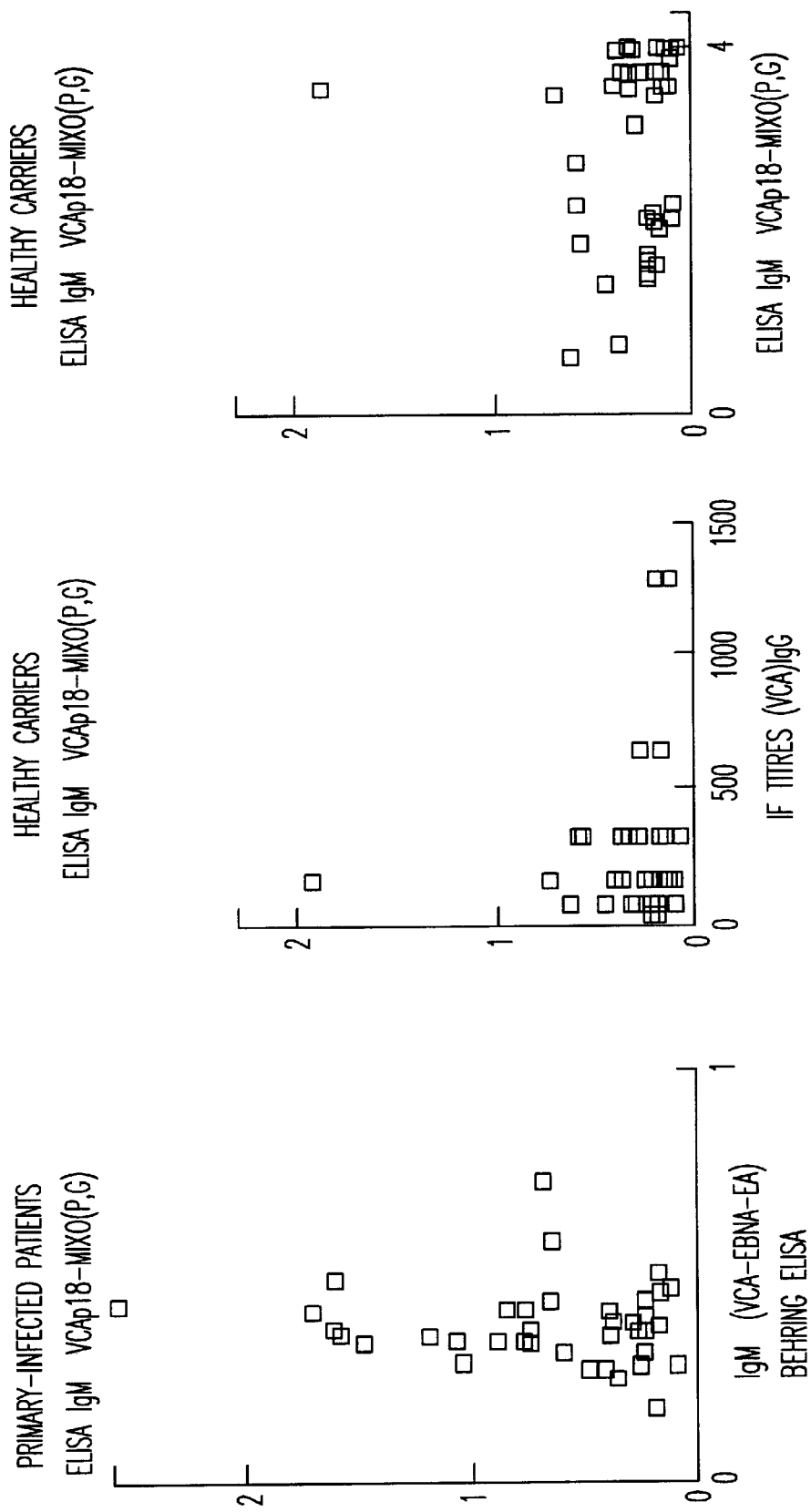

| parent a.a. | A | C | D | E | F | G | H | I | K | L | M | N | P | Q | R | S | T | V | W | Y | parent a.a. |
|---|---|---|---|---|---|---|---|---|---|---|---|---|---|---|---|---|---|---|---|---|---|
| A | 100 | 6 | 17 | 11 | 11 | 50 | 0 | 11 | 6 | 11 | 33 | 22 | 17 | 17 | 0 | 50 | 22 | 28 | 0 | 0 | A |
| C | 7 | 100 | 7 | 15 | 16 | 7 | 13 | 29 | 7 | 10 | 20 | 13 | 7 | 12 | 27 | 7 | 7 | 5 | 7 | 14 | C |
| D | 12 | 38 | 100 | 50 | 4 | 6 | 23 | 18 | 10 | 4 | 12 | 42 | 4 | 12 | 0 | 27 | 15 | 0 | 19 | 0 | D |
| E | 21 | 15 | 42 | 100 | 2 | 13 | 8 | 6 | 6 | 8 | 21 | 13 | 13 | 33 | 4 | 15 | 10 | 6 | 8 | 6 | E |
| F | 11 | 16 | 16 | 11 | 100 | 0 | 5 | 16 | 5 | 37 | 11 | 11 | 11 | 11 | 5 | 32 | 26 | 16 | 8 | 21 | F |
| G | 24 | 3 | 6 | 3 | 6 | 100 | 12 | 6 | 12 | 6 | 15 | 3 | 0 | 9 | 18 | 24 | 3 | 3 | 3 | 3 | G |
| H | 0 | 13 | 23 | 8 | 5 | 23 | 100 | 0 | 15 | 26 | 8 | 15 | 23 | 23 | 23 | 8 | 15 | 8 | 8 | 8 | H |
| I | 47 | 29 | 18 | 29 | 35 | 0 | 0 | 100 | 24 | 59 | 18 | 12 | 6 | 29 | 24 | 24 | 24 | 65 | 6 | 0 | I |
| K | 16 | 0 | 10 | 0 | 10 | 10 | 26 | 13 | 100 | 10 | 32 | 23 | 3 | 26 | 39 | 29 | 23 | 13 | 6 | 0 | K |
| L | 12 | 10 | 8 | 2 | 22 | 2 | 8 | 49 | 18 | 100 | 29 | 6 | 4 | 12 | 10 | 4 | 4 | 22 | 6 | 10 | L |
| M | 33 | 20 | 12 | 21 | 11 | 15 | 8 | 18 | 18 | 29 | 100 | 13 | 11 | 13 | 17 | 22 | 24 | 5 | 4 | 14 | M |
| N | 22 | 4 | 27 | 4 | 4 | 20 | 39 | 49 | 9 | 4 | 13 | 100 | 11 | 13 | 17 | 44 | 11 | 10 | 4 | 0 | N |
| P | 24 | 8 | 6 | 17 | 8 | 18 | 9 | 18 | 16 | 33 | 16 | 25 | 100 | 16 | 5 | 15 | 10 | 10 | 8 | 10 | P |
| Q | 20 | 15 | 0 | 15 | 5 | 6 | 19 | 15 | 5 | 6 | 25 | 17 | 10 | 100 | 10 | 28 | 3 | 10 | 10 | 10 | Q |
| R | 67 | 27 | 19 | 6 | 14 | 3 | 8 | 52 | 67 | 33 | 67 | 9 | 33 | 33 | 100 | 44 | 22 | 33 | 33 | 33 | R |
| S | 33 | 11 | 0 | 8 | 16 | 3 | 8 | 6 | 11 | 6 | 22 | 12 | 6 | 15 | 28 | 100 | 29 | 6 | 17 | 6 | S |
| T | 12 | 6 | 27 | 6 | 14 | 3 | 8 | 14 | 12 | 9 | 24 | 14 | 14 | 12 | 3 | 44 | 100 | 21 | 15 | 14 | T |
| V | 24 | 5 | 6 | 8 | 16 | 3 | 8 | 52 | 10 | 33 | 5 | 4 | 8 | 10 | 10 | 5 | 15 | 100 | 14 | 14 | V |
| W | 0 | 7 | 0 | 6 | 29 | 3 | 8 | 6 | 6 | 6 | 0 | 0 | 0 | 10 | 33 | 17 | 6 | 14 | 100 | 14 | W |
| Y | 14 | 14 | 0 | 6 | 29 | 3 | 8 | 0 | 14 | 14 | 14 | 0 | 14 | 10 | 14 | 6 | 6 | 14 | 14 | 100 | Y |

FIG. 16

REAGENT FOR DETECTING AND MONITORING VIRAL INFECTIONS

The present invention relates to a reagent for detecting and monitoring viral infections, such as those caused by the Epstein-Barr virus or EBV, which is in particular the causative agent of infectious mononucleosis, by the hepatitis C virus (HCV) or by the human immunodeficiency virus (HIV) and to its applications for the detection of a viral infection, in particular of an EBV infection, at any stage of the infection (primary infection, healthy carriers and induced tumours).

EBV is a herpesvirus which preferably infects the B lymphocytes and the epithelial cells.

This lymphocryptic virus escapes immunological surveillance. In general, the virus is carried by healthy carriers, with no special symptoms; however, under immunodeficient conditions, such as AIDS or chemotherapy following a transplant, as well as in endemic regions, such as in Africa or in Asia, the oncogenic potential of EBV is freed and leads to the emergence of various tumours, such as African Burkitt's lymphoma, undifferentiated carcinoma of the nasopharynx, certain lymphomas and Hodgkin's disease.

At present the serodiagnosis of EBV is carried out either by the Paul-Bunnell reaction (detection of heterophilic antibodies), a simple and rapid but nonspecific method (LINDERHOLM M. et al., *J. Clin. Microbiol.*, 1994, 32, 1, 259–261), by immunofluorescence (IF) tests which are specific for each class of antigens (VCA, EA and EBNA).

The development of a simpler and less expensive diagnostic test using an immunoenzymatic method such as the ELISA method is in this context particularly desirable and several tests have thus been proposed (M. GORGIEVSKY-HRISOHO et al., *J. Clin. Microbiol.*, 1990, 28, 2305–2311; J M. MIDDELDORP et al., *J. Virol. Methods*, 1988, 21, 133–159).

The immunoenzymatic methods proposed in the prior art exhibit, for the majority, the major disadvantage of lacking detection sensitivity (M. GORGIEVSKY-HRISOHO et al., cited above; J M. MIDDELDORP et al., cited above). To solve this problem of lack of sensitivity, some authors have proposed using various antigens, in combination; such combinations increase the sensitivity of the test in which these combinations are used, but not the specificity. The combinations of antigens which have been proposed in the prior art comprise, for example, the antigen p47–52 (major antigen EA-D, encoded by the open reading frame called BMRF1, SWISS-PROT accession No. P03191), the antigen p38 (encoded by the open reading frame called BALF2, SWISS-PROT accession No. P03227) and the antigen gp125 or gp110 (encoded by the open reading frame called BALF4, SWISS-PROT accession No. P03188) (W. M. J. Van GRUNSVEN et al., *J. Virol.*, 1993, 67, 3908–3916).

More recently, it has been shown that an 18 kDa capsid antigen (VCAp18), encoded by the open reading frame BFRF3 (SWISS-PROT accession No. P14348), is recognized by healthy carriers of EBV in immunoblot analysis and appears not to exhibit homologous sequences with the other human herpesviruses, unlike the major proteins, such as VCAp40 (sequence encoded by the open reading frame called BdRF1, SWISS-PROT accession No. P03219) and gp125/110 (R. BAER et al., *Nature*, 1984, 310, 207–211; M. S. CHEE et al., *Curr. Topics Microbiol. Immunol.*, 1990, 154, 125–170; A. J. DAVIDSON, *J. Gen. Virol.*, 1986, 67, 1759–1816). The map of the antigenic domains of the antigen VCAp18 has been established and the major antigenic domain has been localized in the C-terminal region of the protein (W. M. J. Van GRUNSVEN et al., *J. Infect. Dis.*, 1994, 170, 13–18).

However, ELISA tests carried out with this capsid antigen VCAp18 have the disadvantage:

of not exhibiting sufficient sensitivity and specificity to detect all the anti-VCA Ig's produced (false-positives and/or false-negatives); in particular, as regards the false-negatives, they are essentially due to the small size of the synthetic peptide VCAp18/SEQ ID No. 2 (24 amino acids, SEQ ID No. 2 of the sequence listing), which may consequently not be recognized by all the VCA-positive individuals and/or because of the heterogeneity of the reactivity of the antibodies towards the synthetic peptide, compared with the same peptide, in its natural environment, of not allowing differential diagnosis of the various stages of the EBV infection and/or of the pathologies induced by EBV, depending on the isotype profile of the Ig's produced (IgG, IgA and IgM), despite the use of the C-terminal fragment of the VCAp18 protein (SEQ ID No. 1 of the sequence listing), as reagent.

A similar situation is encountered with other viruses, such as HCV or HIV; indeed, in general, the use of one or more immunodominant fragments does not exhibit sufficient sensitivity to avoid false-negatives.

Accordingly, the Applicant company set itself the objective of providing a new reagent for the detection of viral infections, capable of being used in immunoenzymatic tests, which is both specific and sensitive and which makes it possible to obtain a gain in sensitivity of at least 15 to 30% compared with the prior art reagents.

Accordingly, the Applicant company also set itself the objective of providing a new reagent for the detection of EBV infections, capable of being used in immunoenzymatic tests, which is both specific and sensitive and which allows differential diagnosis of the stage of the infection and/or of the pathology, depending on the prevalent isotype; indeed, the presence of human anti-VCA IgMs is essentially the sign of a primary infection, the presence of human anti-VCA IgGs is essentially the sign of a past infection (healthy carriers, generally), whereas the presence of human anti-VCA IgAs suggests the emergence of a tumour. Such a reagent is more suitable for the requirements of practical use than the prior art reagents in the context of immunoenzymatic tests, in particular of the ELISA type.

The subject of the present invention is a reagent for the diagnosis of an infection caused by a virus, characterized in that it comprises essentially a mixture consisting of (1) an immunodominant fragment of a protein of the said virus comprising at most 60 amino acids, preferably between 20 and 30 amino acids and (2) a mixture (called mixotope) of convergent combinatory peptides derived from the said immunodominant fragment, which peptides are obtained by complete or partial artificial degeneration of the said immunodominant fragment by systematic or partial replacement of each amino acid with another according to a suitable replaceability matrix.

For the purposes of the invention, mixotope is understood to mean the mixture of all the combinatory peptides obtained from the selected immunodominant fragment by artificial or constructed degeneration; they are preferably obtained during a single synthesis and represent the peptide antigen and its variability in its antibody population recognition function; various mixotopes may be obtained from the same peptide; the factors which are involved in the constitution of a mixotope are:

on the one hand, the percentage degeneration of the native immunodominant fragment selected (total or partial degeneration); the conserved amino acids (isolated or forming a sequence), in the case of a partial degeneration, are preferably, as regards EBV, those which are involved in the structuring of the VCAp18 protein and on the other hand, the mode of selection of the substitution of the amino acids of the said native immunodominant fragment; for each position of the sequence of the native immunodominant fragment chosen, the amino acid substitution is selected on the basis of the replacement matrix established by H. M. GEYSEN et al., (*J. Mol. Recog.,* 1988, 1, 32–41), or modified, as illustrated in FIG. 16, taking into account the tolerance of the antibody recognition, depending on the amino acid substitution in the linear epitopes: for a given position, the amino acids exhibiting the highest percentage of "replaceability" are preferably chosen. However, it is preferable to take into account the conformation of the natural epitopes, before degeneration.

The mixotope for the purposes of the present invention, consisting of convergent combinatory peptides derived from a native immunodominant fragment, therefore represents an artificial and non-natural degeneration of the native structure by the systematic or partial replacement of each amino acid with another derived from the GEYSEN replaceability matrix or from the matrix according to FIG. 16.

Also for the purposes of the invention, constructed replaceability matrix is understood to mean a matrix which does not reproduce the natural variations or the variations frequently observed in evolution; the GEYSEN replaceability matrix or the matrix according to FIG. 16 are particularly suitable.

Surprisingly, the reagents according to the invention make it possible to obtain reliable, reproducible, very sensitive and very specific results since the combinations according to the invention exhibit a synergistic effect in the detection of the antibodies induced by viruses; in particular, a gain in sensitivity of 15 to 30% is generally obtained regardless of the virus (HIV, HCV, EBV, for example).

The subject of the present invention is also a diagnostic reagent according to the invention, characterized in that, for the diagnosis of EBV infections, it comprises essentially a mixture consisting of (1) a C-terminal fragment of the 18 kDa viral capsid antigen (protein VCAp18, SEQ ID No. 1) of the Epstein-Barr virus (EBV) comprising at most 60 amino acids, preferably between 20 and 30 amino acids and (2) a mixture (called mixotope) of convergent combinatory peptides derived from the said C-terminal fragment or peptide VCAp18.

According to an advantageous embodiment of the reagent according to the invention, the said C-terminal fragment of the VCAp18 protein is selected from the group consisting of the peptides VCAp18/SEQ ID No. 2, VCAp18/SEQ ID No. 3, VCAp18/SEQ ID No. 4 and VCAp18/SEQ ID No. 5.

Unexpectedly, the combination of a C-terminal fragment of the VCAp18 protein with a mixotope, derived from the said fragment, and regardless of the configuration of the C-terminal fragment chosen, significantly enhances the sensitivity and specificity of the immunoenzymatic serodiagnosis of EBV; indeed, if an ELISA test using a reagent according to the invention as defined above is compared with an ELISA test using only a peptide VCAp18, a 100% sensitivity and a 100% specificity are effectively obtained with the reagent according to the invention because of the binding of all the anti-VCA Ig's (G, A and M) to the said reagent.

Surprisingly, the reagents according to the invention make it possible to obtain reliable, reproducible, very sensitive and very specific results because the combinations according to the invention exhibit a synergistic effect in the detection of all the human anti-VCA Ig's produced.

The mixture of degenerate peptides which is artificially produced during the same synthesis is combined with the native peptide. Such a combination makes it possible, unexpectedly, to increase the reactivity of the mixture of antigens which is produced with respect to the antibodies naturally induced by the virus.

Under these conditions, it is possible to obtain sensitivities of the order of 100% and 97%, respectively, in the populations of post-infected and primary-infected subjects, while preserving 100% specificity in all the tests carried out.

For example:

for the peptide VCAp18/SEQ ID No. 2, it is thus possible to obtain the following three mixotopes:

- the mixotope corresponding to a degeneration of the entire sequence of the peptide VCAp18/SEQ ID No. 2, called hereinafter mixotope MIXO,
- the mixotope in which the proline residues of the peptide VCAp18/SEQ ID No. 2 are preferentially conserved, the latter being involved in particular in the conformation; the said mixotope, called hereinafter mixotope MIXO(P), corresponds to a partial degeneration of the sequence of the peptide VCAp18/SEQ ID No. 2 and
- the mixotope in which both the proline residues and the sequence Gly Ser Gly Gly Gly Gly (SEQ ID No. 6) of the peptide VCAp18/SEQ ID No. 2 are preferentially conserved; the mixotope, called hereinafter mixotope MIXO(P,G), corresponds to a partial degeneration of the sequence of the peptide VCAp18/SEQ ID No. 2, for the peptide VCAp18/SEQ ID No. 3, it is thus possible to obtain the following mixotopes:

- the mixotope corresponding to a degeneration of the entire sequence of the peptide VCAp18/SEQ ID No. 3,
- the mixotope in which the proline residue and/or the serine residues of the repetitive sequence of the peptide VCAp18/SEQ ID No. 3 are preferentially conserved; the said mixotope corresponds to a partial degeneration of the sequence of the peptide VCAp18/SEQ ID No. 3,
- the mixotope in which the proline residue and the alanine residues of the repetitive sequence of the peptide VCAp18/SEQ ID No. 3 are preferentially conserved; the said mixotope corresponds to a partial degeneration of the sequence of the peptide VCAp18/SEQ ID No. 3 and
- the mixotope in which both the proline residue, the serine residues and the alanine residues of the peptide VCAp18/SEQ ID No. 3 are preferentially conserved, for the peptide VCAp18/SEQ ID No. 4, it is thus possible to obtain the following mixotopes:

- the mixotope corresponding to a degeneration of the entire sequence of the peptide VCAp18/SEQ ID No. 4,
- the mixotope in which the serine, proline and/or alanine residues and/or the sequence Gly Ser Gly Gly Gly Gly (SEQ ID No. 6) and/or the sequence Ala Ala Ala Ser Ala Ala Ala Ala (SEQ ID No. 7) of the peptide VCAp18/SEQ ID No. 4 are preferentially conserved; the said mixotope corresponds to a partial degeneration of the sequence of the peptide VCAp18/SEQ ID No. 4, for the peptide VCAp18/SEQ ID No. 5, it is thus possible to obtain the following mixotopes:

the mixotope corresponding to a degeneration of the entire sequence of the peptide VCAp18/SEQ ID No. 5, the mixotope in which the serine and/or alanine residues of the peptide VCAp18/SEQ ID No. 5 are preferentially conserved; the said mixotope corresponds to a partial degeneration of the sequence of the peptide VCAp18/SEQ ID No. 5, the mixotope in which both the serine residues and the sequence Ala Ala Ala Ser Ala Ala Ala Ala (SEQ ID No. 7) of the peptide VCAp18/SEQ ID No. 5 are preferentially conserved; the said mixotope corresponds to a partial degeneration of the sequence of the peptide VCAp18/SEQ ID No. 5.

The different mixotopes corresponding to a partial degeneration of the chosen peptide VCAp18 conserve a native sequence which is preferably involved in the structuring of the VCAp18 protein.

According to another advantageous embodiment of the reagent according to the invention, it is attached to a solid support, preferably microtitre plates.

According to another advantageous embodiment of the reagent according to the invention, the C-terminal peptide-:mixotope ratio in the mixture is between 1:10 and 1:100.

The subject of the present invention is also a method for the diagnosis of a viral infection, by an immunoenzymatic method, characterized in that it uses a diagnostic reagent according to the invention.

In particular, as regards EBV infections, the subject of the present invention is also a method of diagnosis by an immunoenzymatic method, characterized in that it comprises:

bringing a serum to be analysed into contact with a reagent as defined above, the addition of anti-human Ig antibodies coupled to an enzyme, and the qualitative and/or quantitative revealing of the anti-VCA antibodies which may be present in the serum to be analysed by addition of the enzyme substrate.

According to an advantageous embodiment of the said method, it comprises:

the attachment of a reagent according to the invention onto a support, such as a microtitre plate, the addition of the serum to be analysed, the detection of the attachment of the anti-VCA antibodies present in the said serum by addition of anti-human Ig (G-A-M) antibodies coupled to an enzyme, and the qualitative and/or quantitative revealing in a spectrophotometer by addition of the enzyme substrate.

The subject of the present invention is also a method for the surveillance and differential detection of the stages of an EBV infection by an immunoenzymatic method, characterized in that it comprises:

the attachment of a reagent according to the invention onto a support, such as a microtitre plate, the addition of the serum to be analysed, the detection of the attachment of the anti-VCA antibodies, which may be present in the said serum, by the addition of anti-human Ig antibodies coupled to an enzyme, which antibodies are selected from the group consisting of the anti-human IgG antibodies, the anti-human IgM antibodies and the anti-human IgA antibodies, and the qualitative or quantitative revealing in a spectrophotometer by the addition of the enzyme substrate.

The primary infection induces the formation of antibodies directed against the different antigens of EBV; they are in particular the antibodies directed against the viral capsid antigen (VCA), the antibodies directed against the nuclear antigen (EBNA), the antibodies directed against the early antigen (EA) and the antibodies directed against the membrane antigen (MA).

These different antibodies do not appear at the same stage of the infection; in particular, the anti-VCA Ig's are produced very early and remain present during the entire life of the host. This means that the detection of the anti-VCA IgMs and IgGs in the human serum reinforces the diagnostic value (particularly advantageous), in order to establish a primary infection with EBV.

Depending on the isotype of the anti-VCA Ig's which is detected in the serum to be analysed, it is possible to distinguish the healthy carriers of the virus (prevalence of the IgGs), the primary infections (prevalence of the IgMs) or the emergence of a tumour, in particular carcinoma of the nasopharynx (prevalence of the IgAs).

Surprisingly, the reagent according to the invention effectively makes it possible to detect the anti-VCA IgAs.

The subject of the present invention is also a method for the early detection of the cancer of the nasopharynx by an immunoenzymatic method, characterized in that it comprises:

the attachment of a reagent according to the invention onto a support, such as a microtitre plate, the addition of the serum to be analysed, the detection of the attachment of the anti-VCA antibodies, which may be present in the said serum, by the addition of anti-human IgA antibodies coupled to an enzyme, and the qualitative or quantitative revealing in a spectrophotometer by the addition of the enzyme substrate.

The subject of the present invention is, in addition, a kit or box for the diagnosis of a viral infection, characterized in that it comprises at least one diagnostic reagent according to the invention.

In addition to the preceding features, the invention further comprises other features which will emerge from the following description which refers to exemplary embodiments of the method which is the subject of the present invention as well as to the appended drawings, in which:

BRIEF DESCRIPTION OF THE DRAWINGS

FIG. 1B illustrates more particularly the comparison between the anti-VCA IgG titres obtained by an immunofluorescence (IF) test with the absorbance value obtained (A492) with an ELISA test using the peptide SEQ ID No. 2. In FIG. 1B, the symbol -■- represents the EBV-positive SEQ ID No. 2-negative sera. FIGS. 1A and 1C comprise on the x-axis the number of sera and on the y-axis the absorbance at 492 nm, whereas FIG. 1B comprises on the x-axis the IF titres and on the y-axis the absorbance values obtained in ELISA.

FIG. 4 illustrates the effect of the combination peptide VCAp18/SEQ ID No. 2+mixotopes: MIXO (FIG. 4A), MIXO(P) (FIG. 4B) or MIXO(P,G) (FIG. 4C), on the IgG-A-M reactivity of the EBV-positive (-□-) and EBV-negative (-○-) sera in ELISA tests. Each microtitre plate well is sequentially coated with 0.1 μg of peptide VCAp18/SEQ ID No. 2 and with 10 μg of one of the abovementioned mixotopes and brought into contact with the sera.

FIG. 7 represents the Klotz plots illustrating the binding of the antibody of different EBV-positive sera (serum 298 6967, serum 298 7943, serum 299 0723 and serum 299 1372) to solid phases containing the peptide VCAp18/SEQ ID No. 2 (-□-),MIXO (-◆-), MIXO(P) (-▲-) or MIXO(P,G) (-○-).

FIG. 8 illustrates the IgG-A-M reactivity (FIG. 8A) and the separate reactivities of the different G, A and M isotypes (FIG. 8B) of EBV-positive sera (subjects who have previously had an infection, -□-) and of EBV-negative sera (-○-), with respect to the reagent according to the invention VCAp18/SEQ ID No. 2+MIXO(P,G).

FIG. 11 illustrates the IgG-A-M reactivity (FIG. 11A) and the separate reactivities of the different G, A and M isotypes (FIG. 11B) of EBV-positive sera (primary infection, -□-) and of EBV-negative sera (-○-), with respect to the reagent according to the invention VCAp18/SEQ ID No. 2+MIXO (P,G).

FIG. 12 illustrates the reactivities of the IgM isotype with respect to the reagent according to the invention VCAp18/SEQ ID No. 2+MIXO(P,G) of EBV-positive sera (primary infection, -□-) and of EBV-negative sera (-○-), which are not treated (FIG. 12A), or which are treated with anti-IgG antibodies (FIG. 12B) or treated by preadsorption of the IgGs (FIG. 12C).

FIG. 13 illustrates the comparison of the IgM reactivity of sera from primary-infected patients with respect to the reagent according to the invention VCAp18/SEQ ID No. 2+MIXO(P,G) with a Behring ELISA test for the detection of the anti-(VCA-EBNA-EA) IgGs.

FIG. 14 illustrates the comparison of the detection of the IgGs in sera from subjects who have been previously infected, obtained by IFA (FIG. 14A) or by an ELISA test using the reagent according to the invention VCAp18/SEQ ID No. 2+MIXO(P,G) (FIG. 14B) with the IgM reactivity of sera from patients who have previously been infected, obtained with an ELISA test using a reagent according to the invention VCAp18/SEQ ID No. 2+MIXO(P,G).

FIG. 16 illustrates an amino acid replacement matrix modified in relation to that of H. M. GEYSEN (reference cited above) and takes into account the symmetry; the values in bold characters are present in the Geysen matrix, the 0 values which are statistically not significant are kept arbitrarily or replaced by the value obtained by the symmetrical replacement.

Figure 2C:
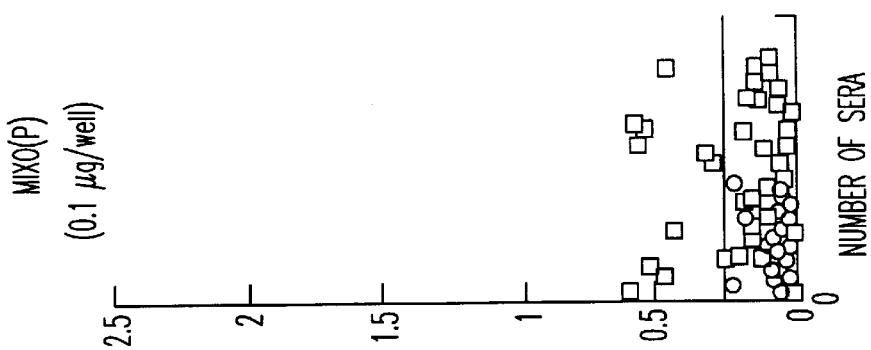
FIG. 2 represents the effect of the mixotopes MIXO, MIXO(P) and MIXO(P,G) on the reactivity of the IgG-A-Ms of the EBV-positive sera (-□-) and the EBV-negative sera (-○-) at two different concentrations: 0.1 μg/well (FIGS. 2A, 2C and 2E) or at 10 μg/well (FIGS. 2B, 2D, 2F), in an ELISA test. The horizontal line represents the cut-off value corresponding to the mean of the control sera+3 SD. These different figures comprise on the x-axis the number of sera and on the y-axis the absorbance at 492 nm.

It should be clearly understood, however, that these examples are given solely by way of illustration of the subject of the invention and do not constitute in any manner a limitation thereto.

EXAMPLE 1

Preparation of the Reagents According to the Invention a) Synthesis of the Peptide The peptide VCAp18/SEQ ID No. 2 is synthesized using the conventional solid phase strategy of the Boc-benzyl (or Fmoc) type, in an automated peptide synthesizer (model 430A, Applied Biosystems Inc.). The groups for protecting the side chains are the following: Asn (Trt), Gln (Trt), Asp (OChx), Glu (OChx), Ser (Bzl), Thr (Bzl), Arg (Tos), Cys (4-MeBzl) and His (Dnp) (see R. C. SHEPPARD, Peptide, Synthesis, Comp. Org. Chem., 1979, 5, 321–363).

The amino acids are introduced using the HBTU/HOBt activation protocol with a systematic double coupling with a resin Boc-Gln-Pam (Applied Biosystems). After thiolysis of the dinitrophenyl group Dnp, followed by a final deprotection and a cleavage with hydrofluoric acid, the cleaved and deprotected peptide is precipitated and washed with cold diethyl ether and then dissolved in 5% acetic acid and freeze-dried.

The peptide is purified at more than 90% on a 100 A Nucleosil C18 preparative RP-HPLC column 5 mm×250 mm (Macherey Nagel, Düren, FRG) and the said peptide is then characterized.

The homogeneity is confirmed by analytical HPLC on a Vydac C18 column eluted with a system of solvents (TFA-acetonitrile-water), in a Shimadzu apparatus. The identity is confirmed by the determination of the amino acid composition and by mass spectrometry recorded on a Bio Ion 20 plasma mass spectrometer (Bio Ion AB, Upsala, Sweden) ([M+H]$^-$ calc.: 2494.7; found: 2495.4).

b) Preparation of the Different Mixotopes

These are prepared as described in H. GRAS-MASSE et al., Peptide Research, 1992, 5, 4, 211–216.

Briefly, equimolar quantities of protected amino acids are weighed and are used in the coupling reactions.

To compensate for the differences in kinetics in the reactivities of the different amino acids, a first coupling is carried out with 1 mmol (total quantity) of Boc-amino acid (or of a mixture of Boc-amino acids). A second coupling, using 2 mmol (total quantity) is then systematically carried out. After cleaving with hydrofluoric acid, the crude peptide is dissolved in TFA (30 ml) and precipitated by adding the said peptide to a cold diethyl ether solution (300 ml).

After centrifugation, the precipitate is dissolved in water and freeze-dried. After air-oxidation of the solution at neutral pH, the mixotopes are purified by gel filtration on a TSK HW40S column (Merck, Darmstadt, FRG). An aliquot of each purified imixotope is subjected to total acid hydrolysis for 24 hours with a 6N HCl:phenol (10:1) mixture, for the determination of the amino acid composition.

c) Examples of Different Reagents in Accordance with the Invention

The sequence of the peptide SEQ ID No. 2 and of the mixotopes which are derived therefrom are represented in Table I below.

TABLE I

| Antigen | Sequence | Number of peptides |
|---|---|---|
| VCAp18 (SEQ ID No. 2) | CAVDTGSGGGGQPHDTAPRGARKKQ | 1 |
| MIXO | AVDTGSGGGGQPHDTAPRGARKKQ<br>C<br>GINSSASSSSNAGNSGAKSGKRRN | 16 777 216 |
| MIXO(P) | AVDTGSGGGGQ HDTA RGAKKKQ<br>C               P       P<br>GIESSHSSSSN GESG KSCKRRN | 4 194 304 |
| MIXO(P,G) | AVDT       Q HDTA RGARKKQ<br>C    GSGGGG P     P<br>GIES      N GESG KSGKRRN | 65 536 |

Reagent 1: peptide SEQ ID No. 2+mixotope MIXO mixture (complete degeneration of the structure as presented in Table I above), Reagent 2: peptide SEQ ID No. 2+mixotope MIXO(P) mixture, Reagent 3: peptide SEQ ID No. 2+mixotope MIXO(P,G) mixture.

These reagents are preferably attached to a solid support (microplate) at a concentration of 0.1 µg/well, for the peptide VCAp18/SEQ ID No. 2 and at a concentration of 10 µg/well for the mixotopes.

EXAMPLE 2

Immunoenzymatic Test Using a Reagent According to the Invention for the Serodetection of EBV A. Materials and Methods

ELISA

Microtitre plate wells (Nunc, Maxisorp, Rocksilde, Denmark) are coated overnight at 4° C., either with 0.2 ml of peptide VCAp18/SEQ ID No. 2, or with a mixotope (0.5 µg/ml in 50 mM of NaHCO$_3$, pH 9.6), or sequentially with 0.2 ml of peptide VCAp18/SEQ ID No. 2 (0.5 µg/ml) and 0.2 ml of mixotope (50 µg/ml).

Each well is then washed with a 0.01 M phosphate buffer comprising 1.8% NaCl, pH 7.4 (PBS) and the binding sites in excess are blocked with albumin (addition of 0.3 ml of 2% BSA (bovine serum albumin) in PBS, at 37° C., for 60 minutes).

After 3 washes with 0.3 ml of PBS 0.5%-Tween 20 (Sigma) (PBS-T buffer), the human sera to be tested are diluted 1/50 in PBS-T comprising 2% bovine serum albumin (BSA) and are incubated in wells containing the reagent according to the invention as specified above, for 120 minutes at 37° C., in a humidified atmosphere.

After 4 washes, the peroxidase-goat antibody anti-human IgG-A-M conjugates (diagnostic Pasteur), diluted 1/10,000 in PBS-T buffer comprising 2% BSA, are incubated for 60 minutes at 37° C.

The conjugated antibody, which binds to the Ig's attached to the support, is revealed for its peroxidase activity, using as substrate o-phenylenediamine dihydrochloride and $H_2O_2$, in a 0.05 M citrate buffer, pH 5.5, for 30 minutes in the dark and at room temperature.

The reaction is blocked by the addition of 4N $H_2SO_4$ (50 µl). The absorbance is recorded against a blank at 492 nm ($A_{492}$), with a multichannel automated reader ($M_R$ 5000, Dynatech).

The mean $A_{492}+3$ standard deviations (SD) of the EBV-negative samples is used as cut-off value in the ELISA tests.

Measurement of the Binding Affinity to the Antibody

The specificity of the binding of the positive sera to the different mixotopes in solid phase is evaluated by the absorption of the antibodies by the native antigen VCAp18/SEQ ID No. 2 in solution, using the method of B. FRIGUET et al. (J. Immunol. Methods, 1985, 77, 305–319).

This method is based on the measurement of the free antibody concentration by an indirect ELISA method when the antigen VCAp18/SEQ ID No. 2 and the antibodies are in equilibrium in solution.

The antigen VCAp18/SEQ ID No. 2, at different concentrations ($10^{-10}$ M to $2\times10^{-6}$ M), is first incubated in solution (PBS-T buffer+2% BSA) with an EBV-positive serum, at a constant concentration (1/50) until the equilibrium state is reached.

After incubating for 18 hours at 4° C., 200 µl of each mixture is transferred and incubated for 60 min at 20° C. in the wells of a microtitre plate, previously coated with peptide VCAp18/SEQ ID No. 2 (0.2 ml, corresponding to 0.5 µg/ml) or a mixotope (50 µ/ml, 0.2 ml), in 50 mM NaHCO₃, pH 9.6.

After washing with PBS-T buffer, the bound immunoglobulins are detected by addition of peroxidase-coupled goat antibodies anti-human IgG-A-Ms.

The conjugated antibody, which binds to the Ig's, is revealed by the peroxidase activity as described above. This method gives the displacement curves for the A/Ao bond relative to log(ao). A precise estimation of the mean affinity of the serum containing the anti-VCAp18 antibodies is given by the equation Ao/(Ao–A)=1/v=1+Kd/ao, in which ao is the total soluble antigen concentration, A and Ao are the absorbance values at 492 nm with or without blocking antigen, respectively, and v is the bound antibody fraction, if the different conditions set out in FRIGUET et al. are satisfied.

B. Results a) Binding Serum Antibodies—C-terminal Domain of the Peptide VCAp18/SEQ ID No. 2 (ELISA VCAp18/SEQ ID No. 2)

The reactivity of the anti-VCA human IgG-M-As with respect to the peptide VCAp18/171–194 is analysed by an ELISA test, on different sera: 46 EBV-positive sera, and 28 EBV-negative sera, selected after carrying out a Behring ELISA test and confirmed by IFA (detection of the anti-VCA IgGs, Immunoconcept, USA).

As specified in W. M. J. Van GRUNSVEN, J. Infect. Dis., 1994, 170, 13–19, the C-terminal domain of the VCAp18 protein shows a high immunoreactivity (FIG. 1A).

When it coats microtitre plates at a concentration of 0.1 µg/well, this peptide VCAp18/SEQ ID No. 2 is recognized by the antibodies of most of the EBV-positive sera.

Figures 1, 7A:
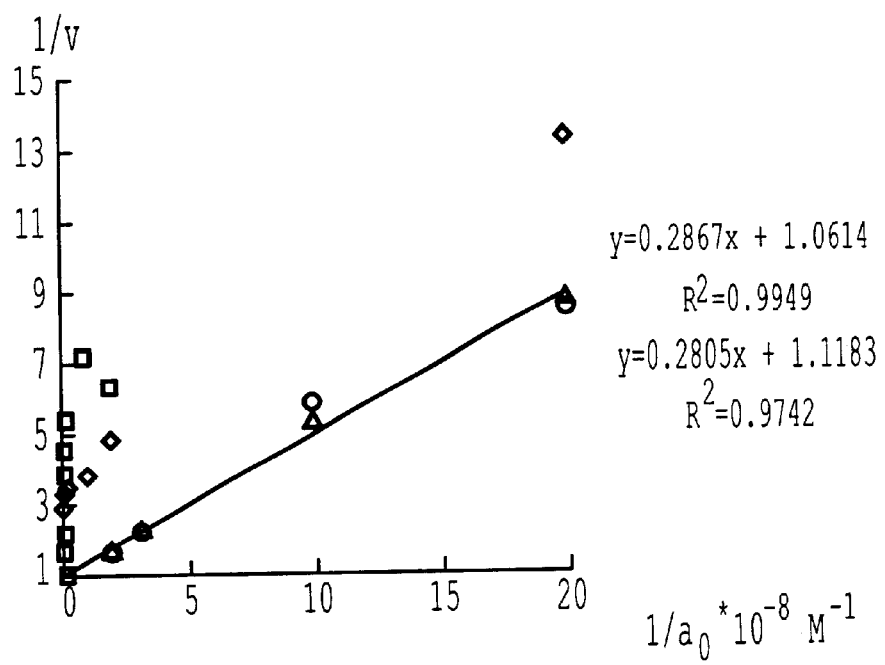
FIG. 1 illustrates the reactivity of the Ig-G-A-Ms of 46 EBV-positive sera (-□-) and 28 EBV-negative sera (-O-) characterized by immunofluorescence with the peptide SEQ ID No. 2 attached onto a solid support in an amount of 0.1 µg/well (FIGS. 1A and 1B) or in an amount of 1 µg/well (FIG. 1C). The horizontal line represents the cut-off value, corresponding to the mean obtained with the negative (EBV-negative) sera+3 standard deviations (SD).

Using 3 standard deviations above the mean value obtained with the control negative sera as lower limit of detection, a high binding sensitivity (89%) and an optimal specificity (100%) are observed in the analysis of the anti-VCAp18 response (FIG. 1A).

To evaluate the possibility of increasing the sensitivity of the test, as a function of the quantity of peptides covering the plates, another concentration was tested for the coating (quantity coating the plates) namely 1 µg/wells; in such a case, a decrease in specificity to 89% is observed (FIG. 1C).

Comparison of the IF titres and of the absorbance values obtained in ELISA, for each serum, does not show any clear correlation, essentially because of a high variability of the absorbance values obtained in ELISA for the sera having intermediate or low IF titres (FIG. 1B).

The EBV-positive sera, which escape detection by ELISA (-■- in FIG. 1B), show IF titres which are detectable at the $160^{th}$ or at the $320^{th}$ (limiting dilutions), confirming that the VCA antigen is effectively recognized by these four peptide VCAp18-negative sera.

b) Binding Serum Antibodies Mixotopes (ELISA VCA Mixotope)

Figures 2, 7A:
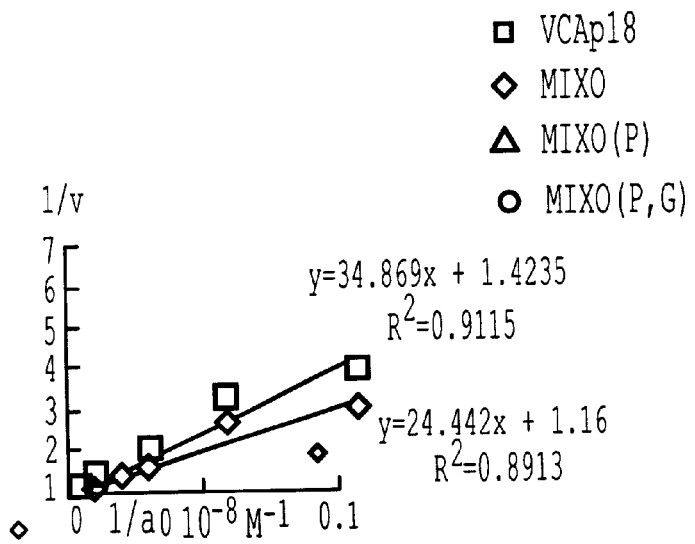
Figures 1, 7B:
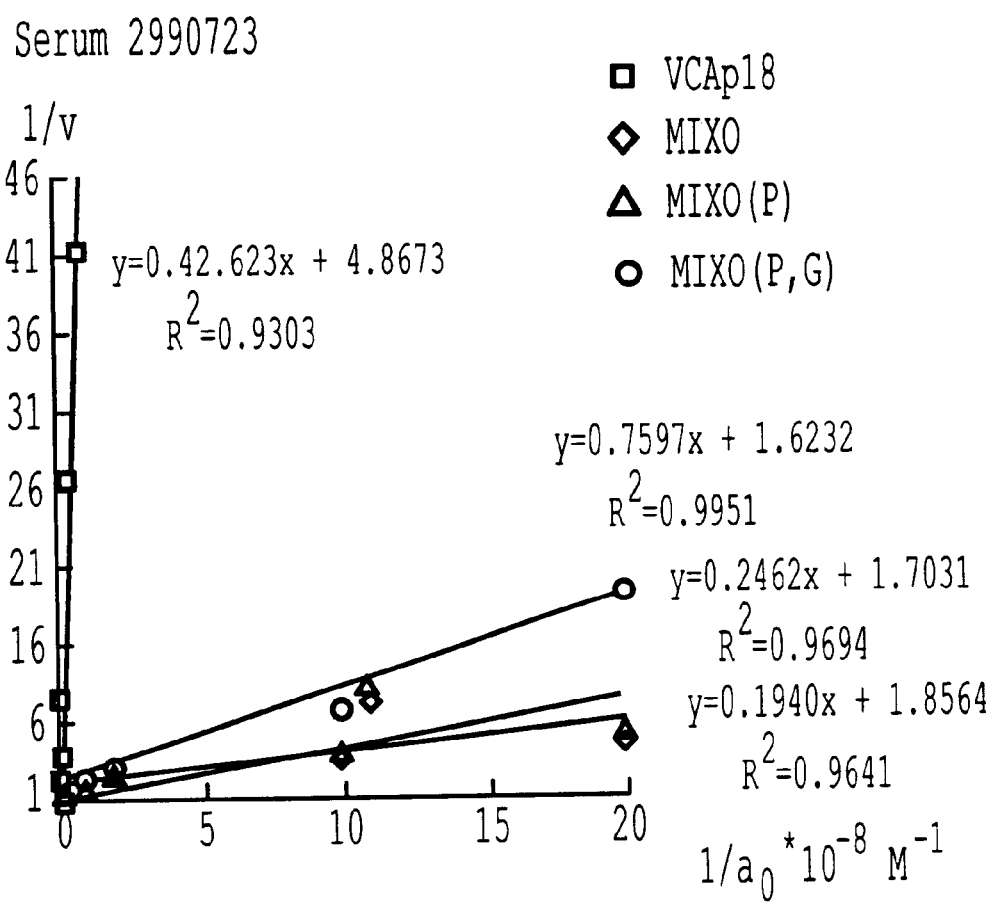
Figures 1, 7C:
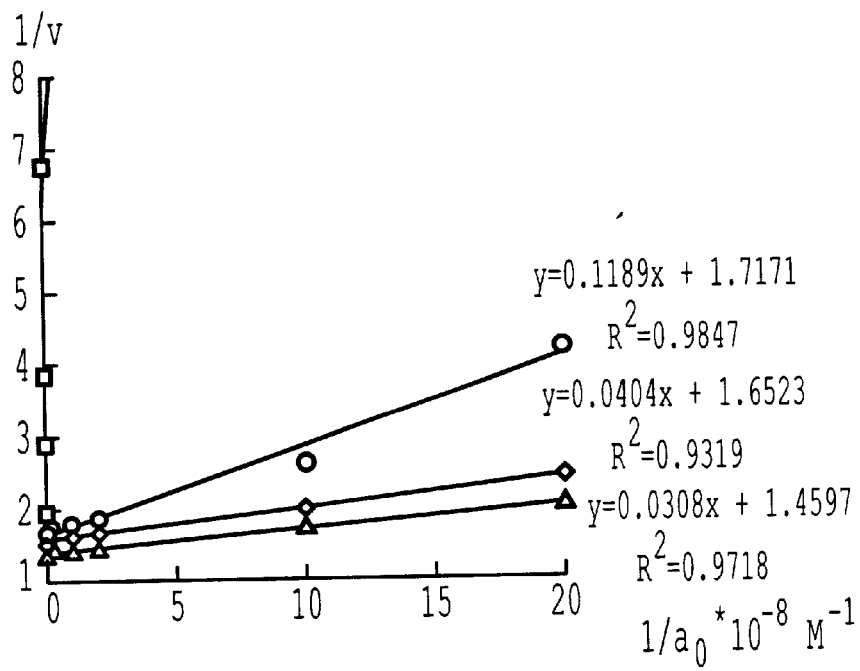
Figures 2, 7C:
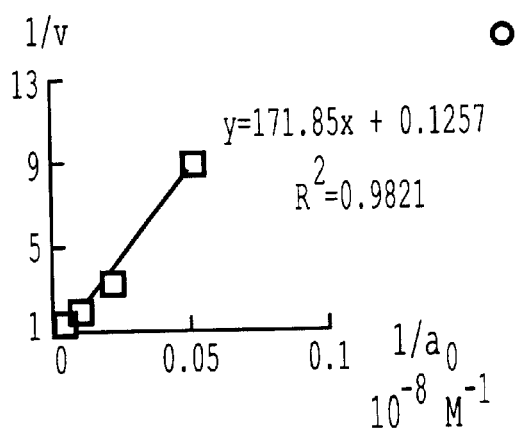
Figures 1, 7D:
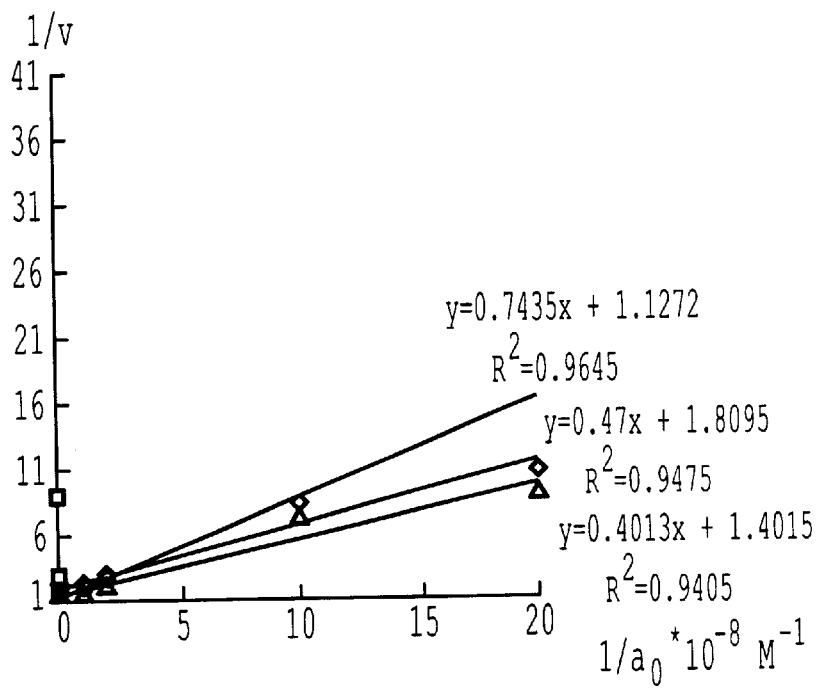
Figures 2, 7D:
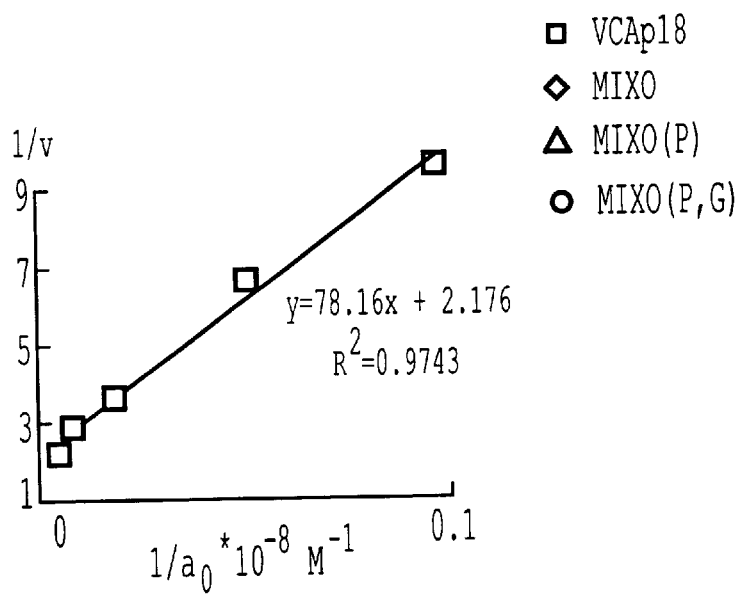

The mixotopes were tested as antigens in solid phase, at two concentrations, namely 0.1 µg and 10 µg/well (FIG. 2).

Figure 2B:
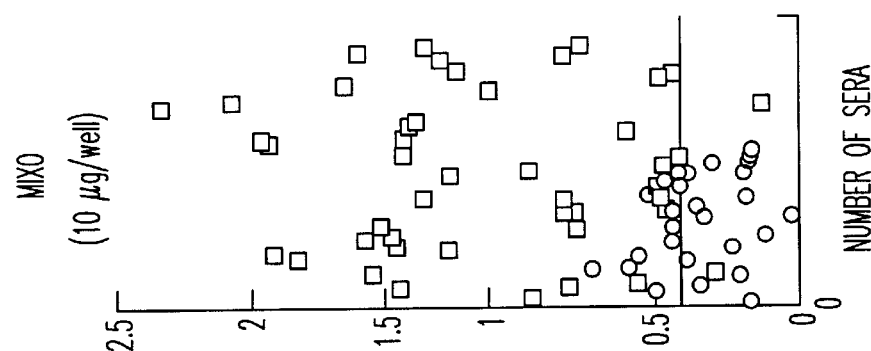
Figure 2A:
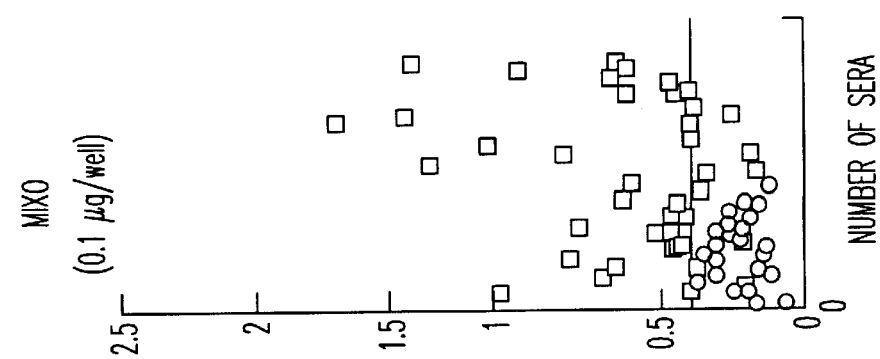
Figure 2F:
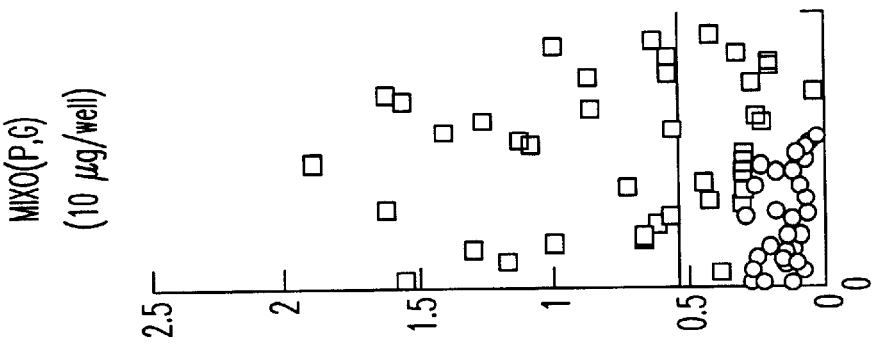
Figure 2E:
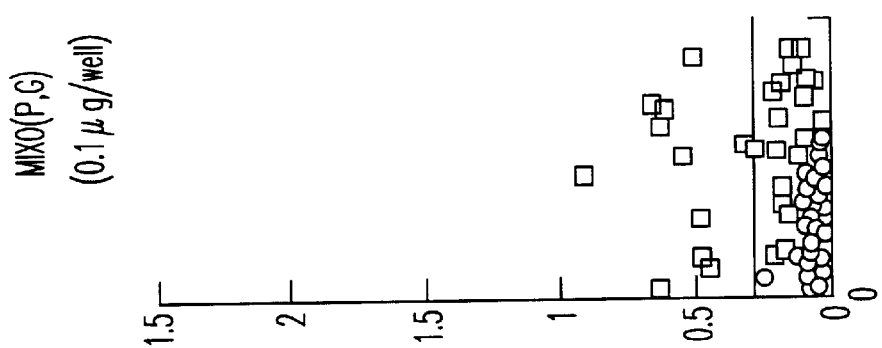
Figure 2D:
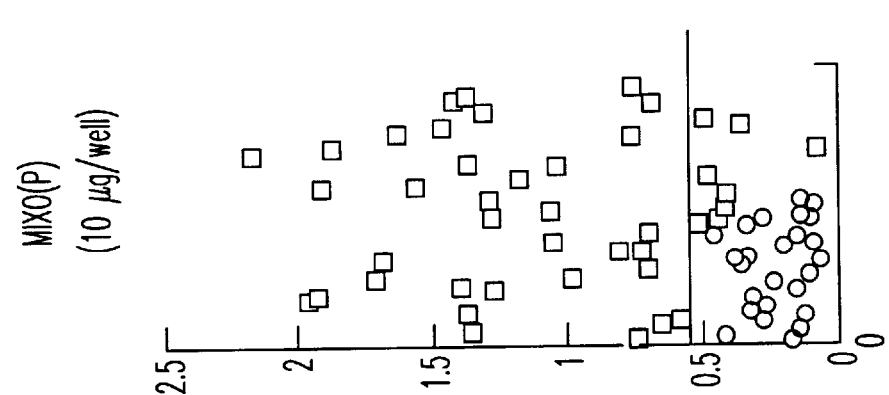
Figure 3A:
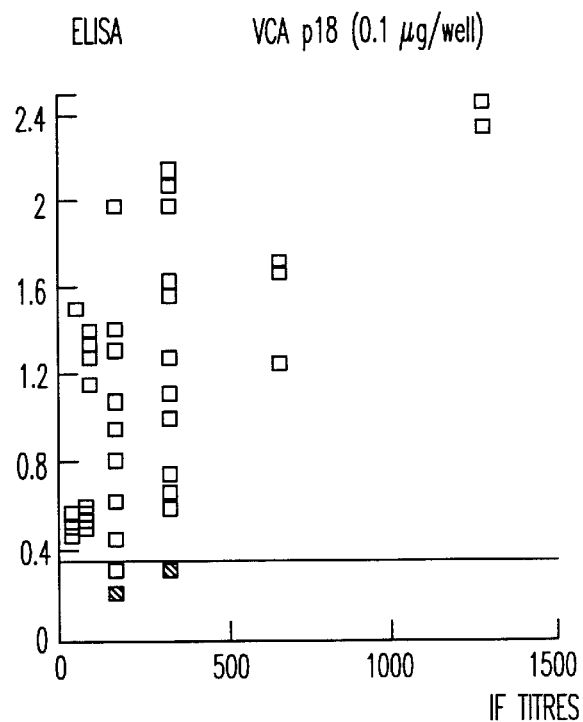
FIG. 3 illustrates the comparison of the behaviours of EBV-positive sera with respect to the peptide VCAp18/SEQ ID No. 2 (FIG. 3A) and the different mixotopes: MIXO (FIG. 3B), MIXO(P) (FIG. 3C), MIXO(P,G) (FIG. 3B); the false-negatives obtained with the peptide VCAp18/SEQ ID No. 2 (FIG. 3A, -■-) define the cut-off value. The data in these FIG. 3 represent the absorbance values obtained by ELISA for all the EBV-positive sera, as a function of their IFA titre. The peptide VCAp18/SEQ ID No. 2 and the mixotopes are used in solid phase respectively at the concentrations of 0.1 and 10 μg/well.
Figure 3B:
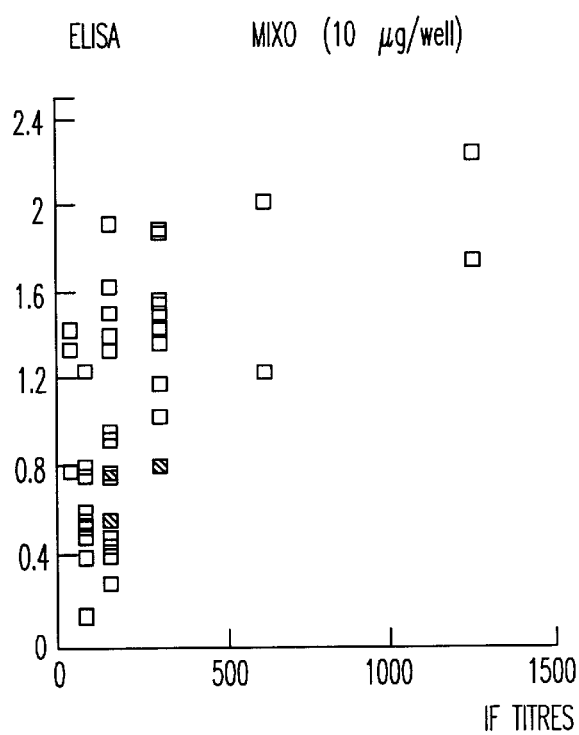
Figure 3C:
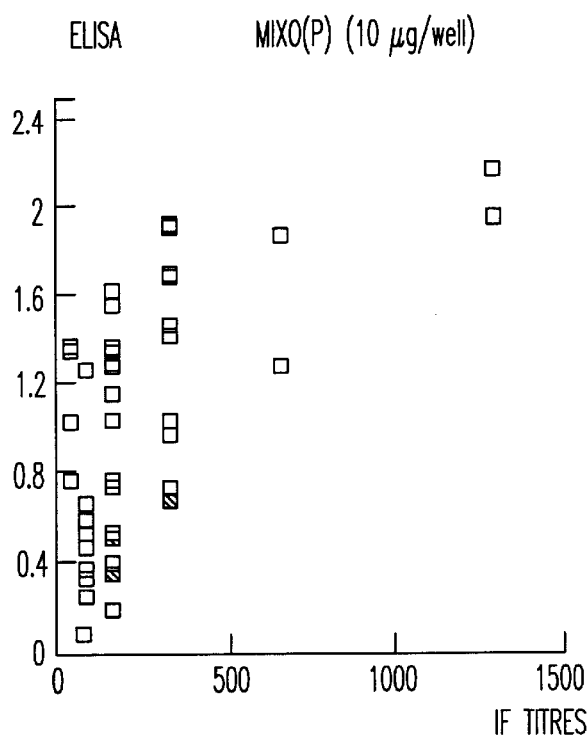
Figure 3D:
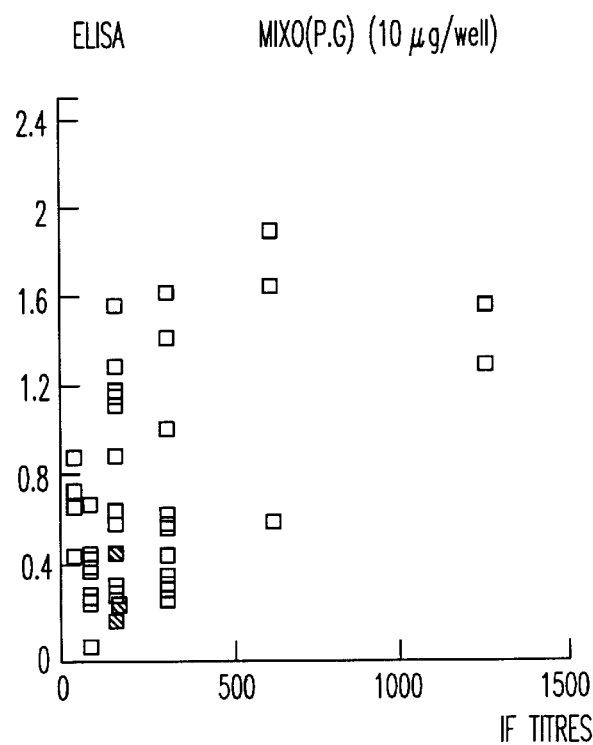

After coating the wells at a concentration of 0.1 µg, the sensitivity is clearly insufficient; only 26, 10 and 10 of the 46 IgG-A-M-positive sera react with MIXO, MIXO(P) and MIXO(P,G) respectively (FIGS. 2A, C, E).

After coating with the mixotopes at a concentration of 10 µg/well, the detection of the positive sera is much more sensitive with an increase in the absorbance values. 46, 36 and 27 of the 46 EBV-positive sera are detected with the mixotopes MIXO, MIXO(P) and MIXO(P,G) respectively (FIGS. 2B, D, F). However, the cut-off value is also higher, because of an increased variation in the absorbance values observed with the negative control sera.

Surprisingly, the loss of binding specificity (11 false-positive sera), is observed only when the antigen MIXO is used (FIGS. 2B, D, F), no false-positive is observed with the other two mixotopes.

Comparison of the IF titres and of the absorbance values obtained in ELISA for each of the 46 IFA-positive sera are illustrated in FIG. 3. The absorbance values observed in ELISA are increased relative to the results obtained with the IF test; these results are particularly advantageous for the sera having low or intermediate IFA titres.

The VCAp18-negative IF-positive tests are symbolized by black squares in FIG. 3.

c) Serum Antibodies-reagent Binding According to the Invention (Combinations Peptide VCAp18/SEQ ID No. 2+Mixotope) (ELISA VCAp18/SEQ ID No. 2+Mixotope)

To show the increase in the sensitivity of detection with the aid of the reagent according to the invention, combinations are used which comprise the peptide VCAp18/SEQ ID No. 2 coating a microtitre plate in an amount of 0.1 µg/well with various mixotopes covering the microtitre plate in an amount of 10 µg/well.

As illustrated in FIGS. 4(A, B, C), all the EBV-positive sera are detected with the three combinations.

A heterogeneity in the results, with the ELISA test, is observed with the EBV-negative sera when the degeneration of the mixotope increases. As illustrated in FIGS. 4A and 4B, the combinations MIXO and MIXO(P) with the peptide VCAp18/SEQ ID No. 2 result in the presence of 4 or 5 false-positive sera. However, the combination with the antigen MIXO(P,G) provides an optimal binding sensitivity (100%) and an optimal specificity (100%) in the VCA-EBV immunoenzymatic serodiagnosis (FIG. 4C).

The results obtained are illustrated in Table II below.

TABLE II

Figure 5A:
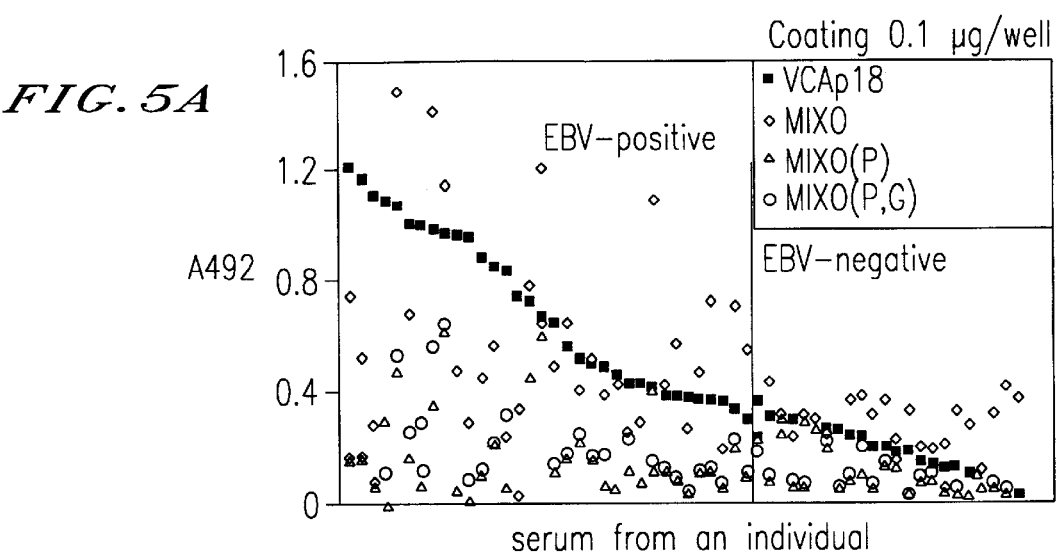
FIGS. 5A and 5B illustrate the variation of the human serological responses of the peptide VCAp18/SEQ ID No. 2 (-■-) and of the abovementioned three mixotopes (MIXO (-◆-) MIXO(P) (-▲-) and MIXO(P,G) (-○-) at two different coating concentrations.
Figure 5B:
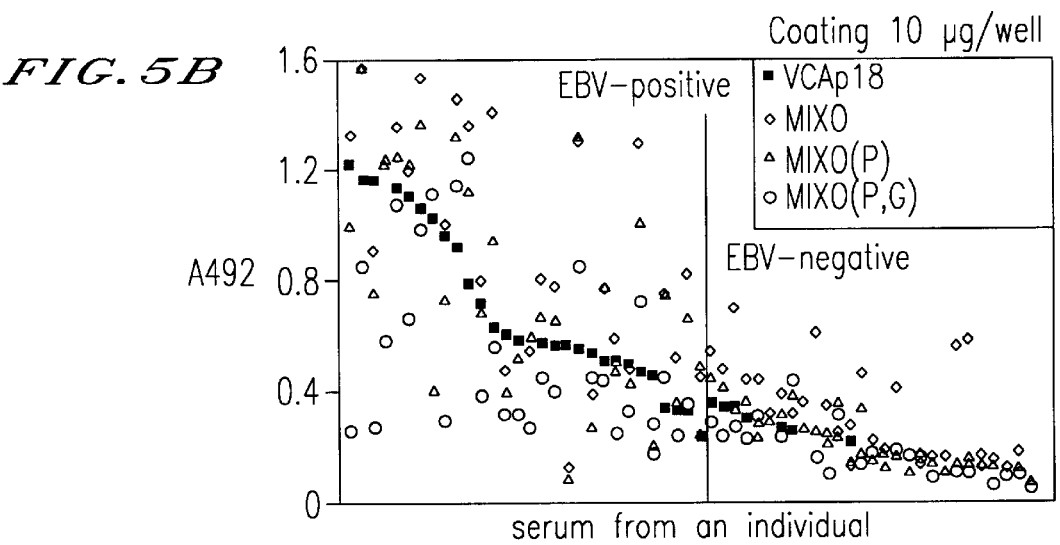

| Antigen solid phase | Coating condition (μg/well) | Detection Ig isotype | Serum N | EBV + | Negative - | Specificity % | Serum N | EBV + | Positive - | Sensitivity % |
|---|---|---|---|---|---|---|---|---|---|---|
| SEQ ID No. 2 | 0.1 | Ig (G-A-M) | 28 | 0 | 28 | 100 | 46 | 42 | 4 | 91 |
|  | 1 | Ig (G-A-M) | 28 | 3 | 25 | 89 | 46 | 44 | 2 | 95 |
| MIXO | 0.1 | Ig (G-A-M) | 28 | 2 | 26 | 92 | 46 | 26 | 20 | 56 |
|  | 10 | Ig (G-A-M) | 28 | 11 | 17 | 60 | 46 | 44 | 2 | 95 |
| MIXO (P) | 0.1 | Ig (G-A-M) | 28 | 0 | 28 | 100 | 46 | 10 | 36 | 21 |
|  | 10 | Ig (G-A-M) | 28 | 0 | 28 | 100 | 46 | 36 | 10 | 78 |
| MIXO (P,G) | 0.1 | Ig (G-A-M) | 28 | 0 | 28 | 100 | 46 | 10 | 36 | 21 |
|  | 10 | Ig (G-A-M) | 28 | 0 | 28 | 100 | 46 | 27 | 22 | 52 |
| SEQ ID No. 2 + MIXO | 0.1 + 10 | Ig (G-A-M) | 28 | 3 | 25 | 89 | 46 | 46 | 0 | 100 |
| SEQ ID No. 2 + MIXO (P) | 0.1 + 10 | Ig (G-A-M) | 28 | 4 | 24 | 85 | 46 | 46 | 0 | 100 |
| SEQ ID No. 2 + MIXO (P,G) | 0.1 + 10 | Ig (G-A-M) | 28 | 0 | 28 | 100 | 46 | 46 | 0 | 100 | d) Relevance of the Combinations of Peptide VCAp18/Mixotopes for the Serodiagnosis of EBV A more detailed analysis of the distribution of the individual responses to the peptide VCAp18/SEQ ID No. 2, to its mixotopes and to their combinations (reagent according to the invention) is illustrated in FIG. 5.

All the sera exhibit an absorbance value of less than 1.3 with an ELISA test using only the peptide VCAp18/SEQ ID No. 2 were selected. Each serum is represented by 4 symbols corresponding to the absorbance values obtained when they are reacted with the different antigens in solid phase.

In some cases, the signal is clearly increased when the mixotopes are used as antigens in solid phase including for the IF-positive-VCAp18/SEQ ID No. 2-negative sera.

Figure 5C:
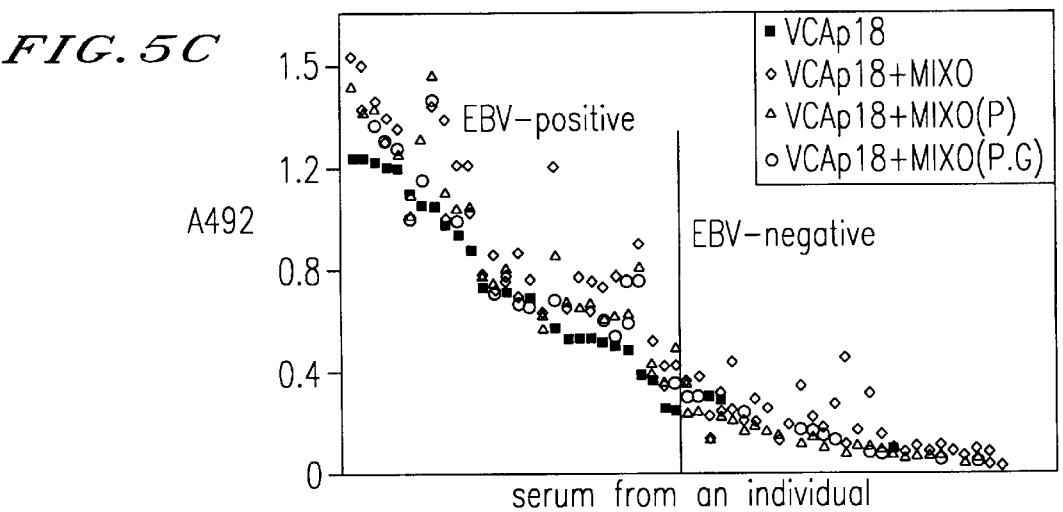
FIG. 5C illustrates the variation of the serological responses of the peptide VCAp18/SEQ ID No. 2 (-■-) and of the abovementioned three mixotopes in combination with the peptide VCAp18/SEQ ID No. 2; VCAp18/SEQ ID No. 2+MIXO (-◆-), VCAp18/SEQ ID No. 2+MIXO(P) (-▲-) and VCAp18/SEQ ID No. 2+(P,G) (-○-). For each experiment, the sera having an absorbance at 492 nm of less than 1.3 with the peptide VCAp18/SEQ ID No. 2 are selected and the vertical line delimits the boundary between the EBV-positive and EBV-negative sera.
Figure 6B:
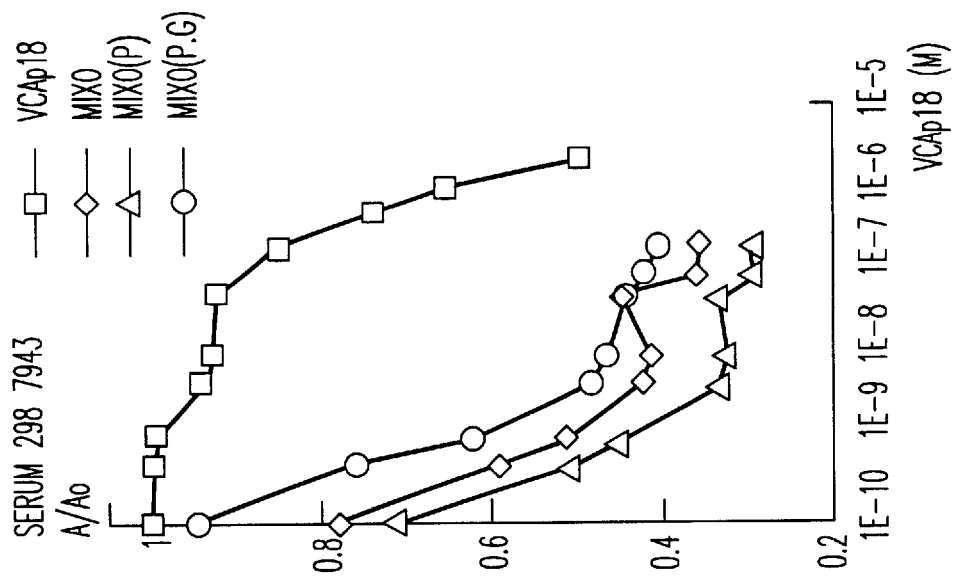
FIG. 6 illustrates the inhibitions of the binding of the antibodies of different EBV-positive sera (serum 298 6967, serum 298 7943, serum 299 0723 and serum 299 1372) to a solid phase containing the peptide VCAp18/SEQ ID No. 2 (-□-), MIXO (-◆-), MIXO(P) (-▲-) or MIXO(P,G) (-○-) by increasing the concentrations of peptide VCAp18/SEQ ID No. 2. This figure comprises on the x-axis the concentration of peptide VCAp18/SEQ ID No. 2 and on the y-axis the A/Ao ratio.
Figure 6A:
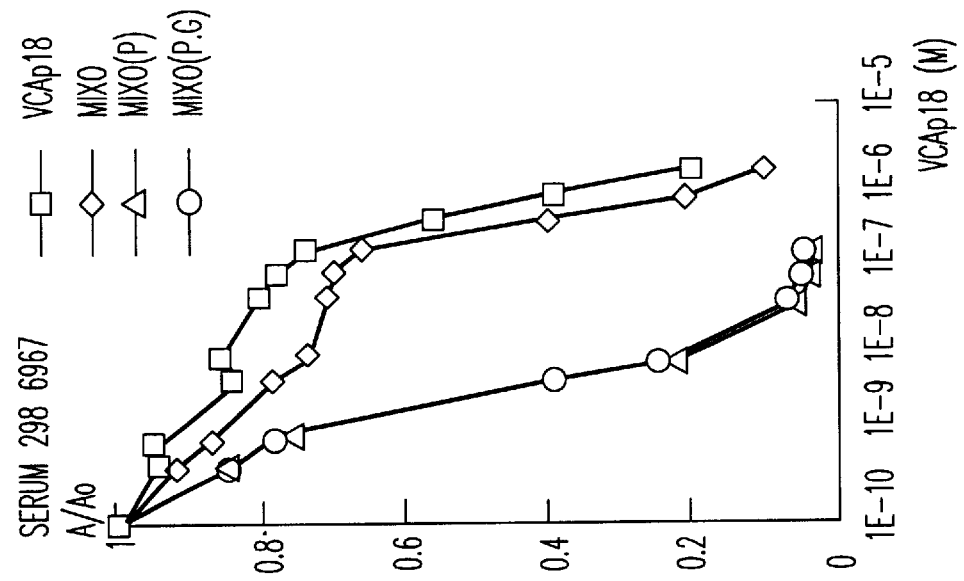
Figure 6D:
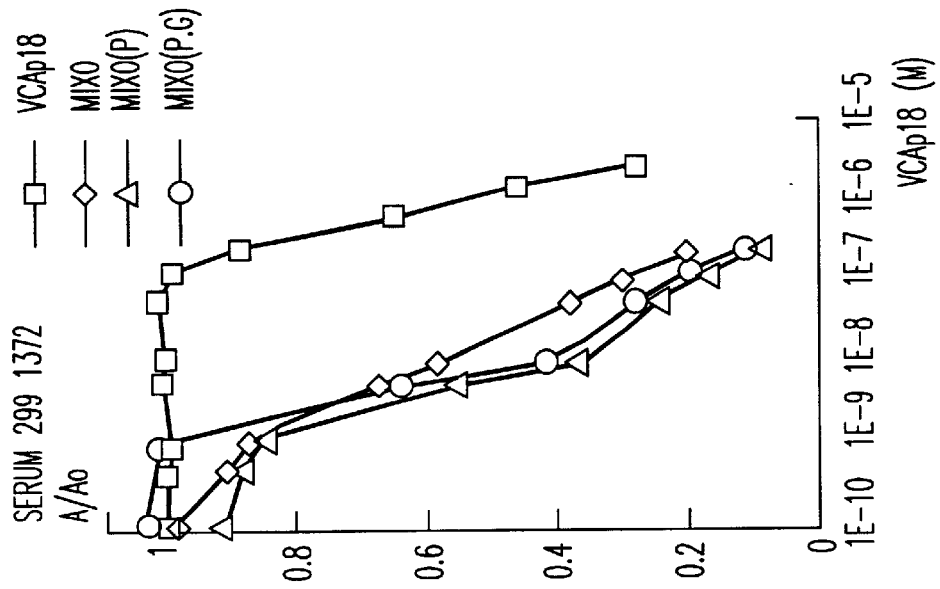
Figure 6C:
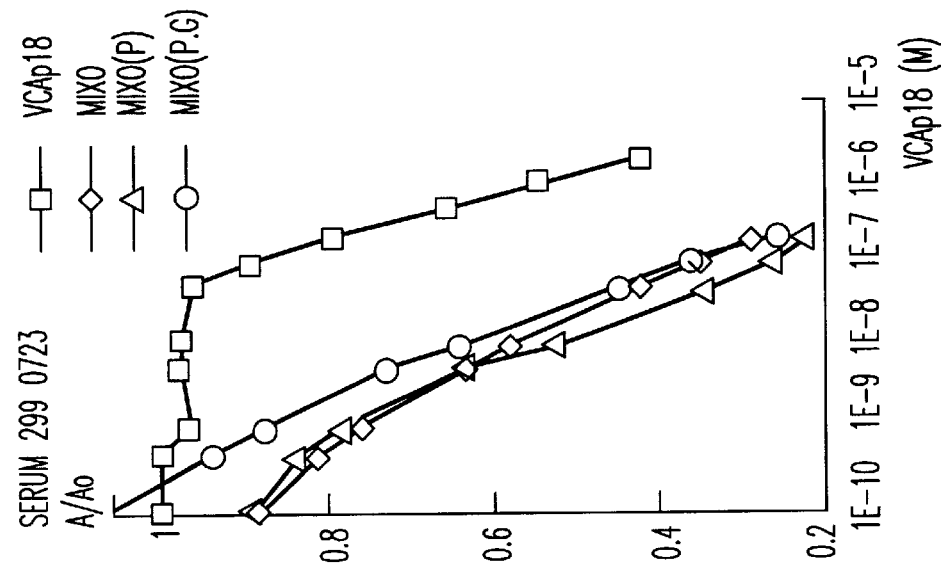

As illustrated in FIG. 5C, almost all the absorbance values obtained when the positive sera are tested with the reagent according to the invention are greater than the absorbance values obtained with the peptide VCAp18/SEQ ID No. 2 alone.

The 3 combinations efficiently detect all the EBV-positive sera, which exhibit a low signal with the mixotopes.

The signal obtained with the sera which are negative with the combinations according to the invention is also generally lower than when these sera are tested with the peptide VCAp18/SEQ ID No. 2 alone, except when the completely degenerate construct MIXO is used.

However, the completely degenerate mixotopes obtained from peptides derived from the C-terminal portion of the VCAp18 protein and containing no proline, for example, effectively confer the desired properties on the reagent according to the present invention.

e) Evaluation of the Avidity of the Mixotopes for the Serum Antibodies Compared with the Peptide VCAp18/SEQ ID No. 2, by ELISA The peptide VCAp18/SEQ ID No. 2 is used in the ELISA inhibition experiments to evaluate its capacity to inhibit the binding of the EBV-positive human sera to the different mixotopes, used in solid phase.

FIG. 6 represents a few inhibition trials.

As illustrated in this FIG. 6, the binding of the human sera to the 3 mixotopes may be specifically and strongly inhibited by increasing the concentrations of peptide VCAp18/SEQ ID No. 2.

In addition, the peptide VCAp18/SEQ ID No. 2 in solid phase and the different mixotopes in solid phase give parallel displacement curves, indicating the presence of a common population of antibodies which is sensitive to the native peptide and to the degenerate peptides.

FIG. 7 represents the Klotz plots for binding to the antibodies of the EBV-positive sera, measured in ELISA by the method of FRIGUET et al., cited above. The values of the dissociation constants are deduced from the linear regression of the results, expressed in FIG. 6. An increase by a factor of 10 to 400 in the affinity constants is observed for the different mixotopes, compared with the peptide VCAp18/SEQ ID No. 2.

The mean Kd value for VCAp18/171–194, MIXO, MIXO (P) and MIXO(P,G) in these experiments is respectively 0.81±0.62 mM, 0.06±0.01 mM, 2.40±1.54 nM and 4.75±3.75 nM.

EXAMPLE 3

Immunoenzymatic Test Using a Reagent According to the Invention for the Differential Serodetection of the Anti-VCA Human IgGs, IgMs and IgAs and its Role in the Diagnosis of Different Pathologies a) Binding Serum Antibodies Reagent VCAp18/SEQ ID No. 2+MIXO(P,G) According to the Invention in Healthy Carriers The reactivity of the anti-VCA human IgG-A-Ms, IgGs, IgAs and IgMs with respect to the reagent according to the invention VCAp18/SEQ ID No. 2+MIXO(P,G), is analysed with the aid of an ELISA test, using the sera characterized in IF as EBV-negative and EBV-positive (46 EBV-positives and 28 EBV-negatives).

The cut-off is defined as three standard variations above the mean value for the EBV-negative sera, determined for each isotype.

With this criterion, no false-positive serum is observed in any ELISA.

As illustrated in Example 1, c) above (see also FIG. 4C), the reagent peptide VCAp18/SEQ ID No. 2+MIXO(P,G), used as antigen in solid phase, shows an optimal binding sensitivity of 100% and a specificity of 100% in the IgG-A-M serological diagnoses of EBV by an immunoenzymatic method.

The same set of sera which are positive by IF was tested for its IgM, IgG and IgA reactivity, with an ELISA test using as reagent a VCAp18/SEQ ID No. 2+MIXO(P,G) mixture.

To carry out the isotype-specific tests, the procedure is carried out as follows:

The procedure is carried out as specified in Example 1, for the preparation of the microtitre plates.

However, before the incubation of the sera to be analysed, under the conditions specified in Example 1, the sera used for the analysis of the IgMs may be treated:

to remove the IgGs (preadsorption of the IgGs or pretreatment with an anti-human IgG serum (Diagnostic Pasteur, Marnes-La-Vallée, France) or in order to resolubilize the IgMs with a solution absorbing the rheumatoid factor (Behringwerke AG, Marburg, Germany), in accordance with the manufacturers' instructions.

For the revealing, the procedure is carried out as follows:

After 4 washes, the conjugates of goat antibodies (also called second antibodies) directed against the human Ig(G-A-M)s, the IgGs, the IgAs and the IgMs (Diagnostic Pasteur, Marnes-La-Coquette, France), diluted 1/10,000 in a PBS-T+2% BSA buffer are incubated for 60 min at 37° C.

The second conjugated antibodies which bind to the serum Ig's attached to the support are revealed as specified in Example 1.

As illustrated in FIG. 8B, all the sera with the exception of 2 react positively with the IgGs; however, these two IgG-negative sera have high IgA and IgM reactivities, as indicated by the black squares in FIG. 8B. These results are in agreement with the 100% binding sensitivity and the specificity obtained in the IgG-A-M test (FIG. 4C or FIG. 8A) and with the fact that the sera from healthy carriers (infected in the past) exhibit a low IgA and IgM reactivity (FIG. 8B).

However, 91% of these sera from subjects who were infected in the past (healthy carriers) are IgM-positive, among which 78% have residual levels of IgM (OD less than 1), compared with the absorbance value obtained for the IgGs; only 39% of the said sera are IgA-negative; this is a surprising result since most of the patients were considered as healthy carriers or as convalescents, that is to say IgM and IgA-negative.

Only one serum was detected as having high levels of IgM and of IgG, whereas it was IgA-negative, probably indicating a reinfected or primary-infected patient.

To show the specificity of the IgM response, the sera from the healthy carriers were treated with IgG-precipitating reagents: serum treated with an anti-IgG serum or with IgM-resolubilizing reagents or reagents allowing decomplexing of the IgMs: serum treated with a solution capable of absorbing the rheumatoid factor.

Figures 9A, 9B, 9C:
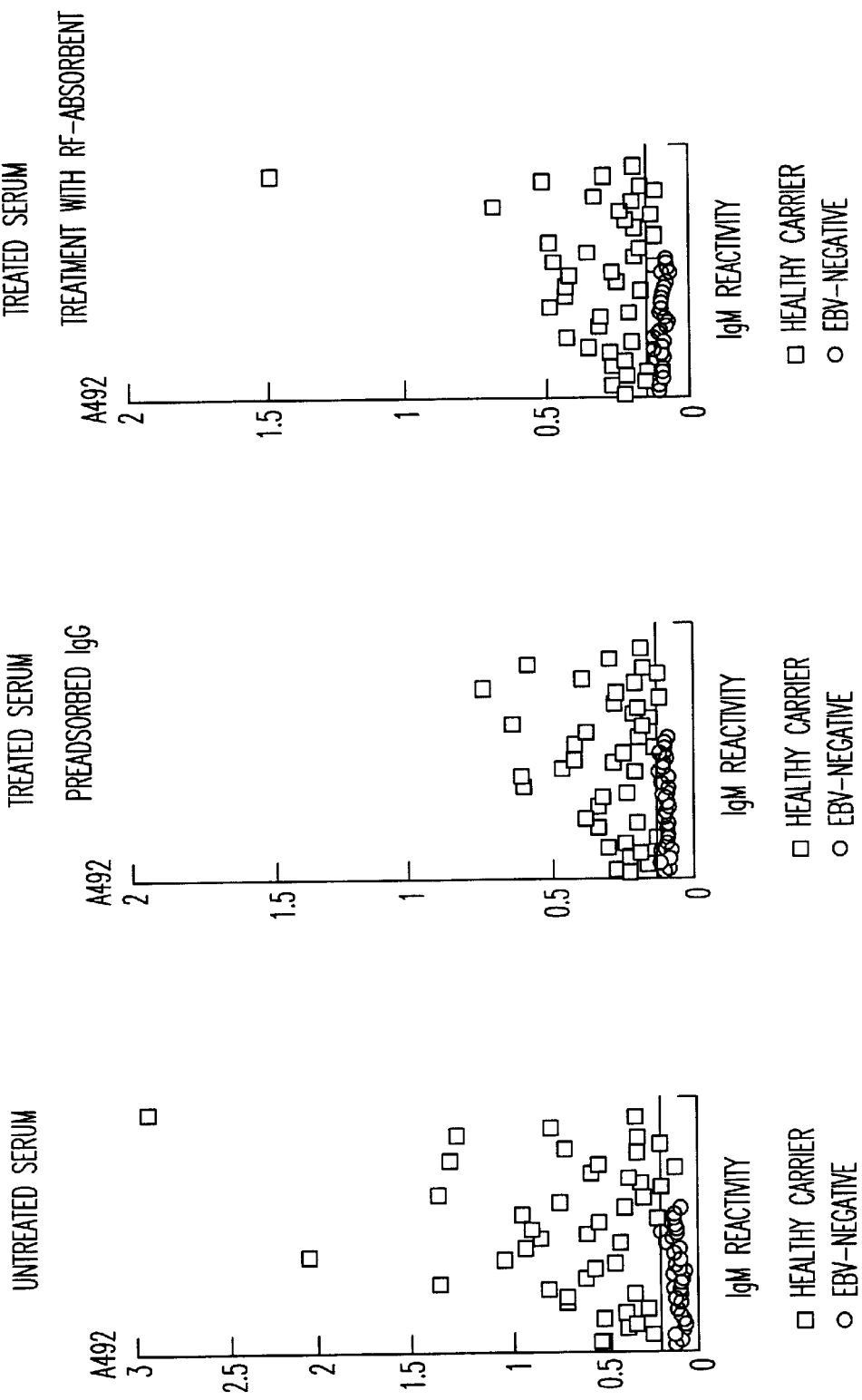
FIG. 9 illustrates the reactivities of the IgM isotype with respect to the reagent according to the invention VCAp18/SEQ ID No. 2+MIXO(P,G) of EBV-positive sera (previous infection, -□-) and of negative sera (-○-), which have not been treated (FIG. 9A), or which have been treated with anti-IgG antibodies (FIG. 9B) or treated by preadsorption of the IgGs (FIG. 9C).

FIG. 9 compares the three ELISAs carried out (untreated serum, serum treated with absorbent and serum treated with anti-IgG serum). No significant difference is detected, a low signal being observed for the ELISA carried out on sera treated with the reagents precipitating the IgGs.

The VCAp18/SEQ ID No. 2+MIXO(P,G) ELISA test for the detection of the Ig(G-A-M)s or of the IgGs were compared in FIG. 10 with a conventional immunofluorescence method using as antigen VCA or a combination VCA-EBNA-EA for the detection of the IgGs in each of the 46 IFA-positive sera (Behring method).

Figure 10A:
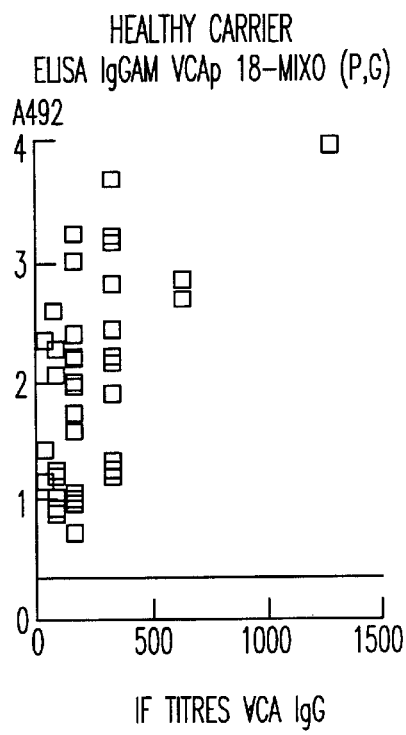
FIG. 10 illustrates the comparison of the IgG-A-M (FIGS. 10A and 10B) and IgG (FIGS. 10C and 10D) reactivities of human sera from patients who have previously had an infection, with respect to the reagent according to the invention VCAp18/SEQ ID No. 2+MIXO(P,G) with an IFA test for the detection of the anti-VCA IgGs and a Behring ELISA test for the detection of the anti-(VCA-EBNA-EA) IgGs. The data represent the absorbance values obtained in ELISA for all the EBV-positive sera, as a function of their IFA titre or the absorbance values obtained with the Behring ELISA test.
Figure 10B:
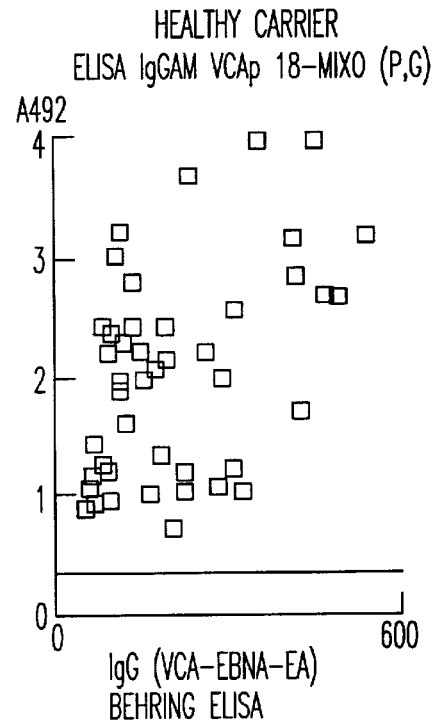
Figure 10C:
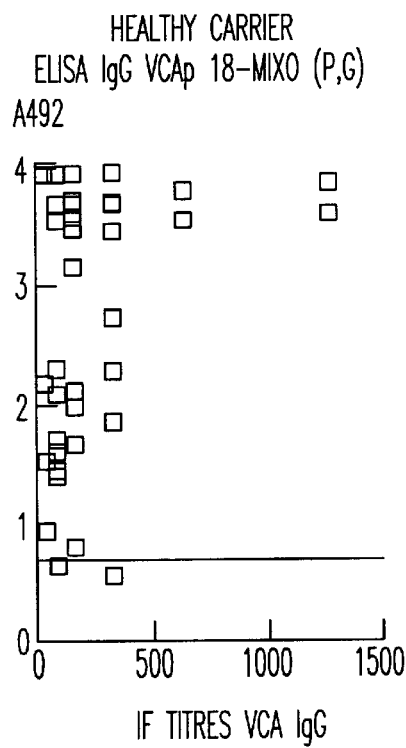

As illustrated in FIGS. 10A and 10C, to high IFA titres correspond high absorbance values with the VCAp18/SEQ ID No. 2+MIXO(P,G) ELISA tests for the detection of the Ig(G-A-M)s or of the IgGs.

Moreover, a high increase in the values obtained with the VCAp18/SEQ ID No. 2–MIXO(P,G) ELISA test is observed with the intermediate and low IF titres.

This situation is particularly important for the detection of the IgG-A-Ms and demonstrates the relevance of the IgG-A-M detection (FIGS. 10A, C).

Figure 10D:
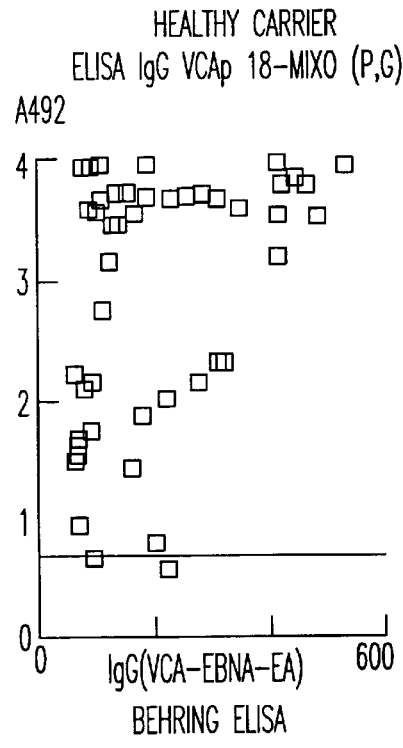

The same type of result is observed in FIG. 10D which compares an ELISA test using the VCAp18/SEQ ID No. 2+MIXO(P,G) reagent and a commercial Behring ELISA, for the detection of the IgGs.

The two EBV-positive sera, which escape detection with the aid of the reagent VCAp18/SEQ ID No. 2–MIXO(P,G), exhibit low or intermediate IF titres ($80^{th}$ and $320^{th}$) and are below the mean value observed in the Behring ELISA test for the detection of the IgGs.

This result is not inconsistent since another set of antigens including EA and EBNA is used in the Behring test.

FIG. 10B compares the VCAp18/SEQ ID No. 2+MIXO (P,G) ELISA test, for the detection of the IgG-A-Ms according to the invention, and the Behring ELISA test, for the detection of the IgGs. No clear correlation is observed between the IgG and IgG-A-M reactivities, suggesting that the combination according to the invention is very specific and contributes to the binding of all the human isotypes, including type M considered as the isotype with the lowest affinity and which is produced right at the beginning of the infection.

b) Study of the Binding of the Serum Antibodies to the Reagent According to the Invention VCAp18/SEQ ID No. 2+MIXO(P,G) in Primary-infected Patients The reactivity of the anti-VCA human IgG-A-Ms, IgGs, IgAs and IgMs with respect to the reagent according to the invention VCAp18/SEQ ID No. 2+MIXO(P,G) is analysed with the aid of an ELISA test, using the 28 EBV-negative sera selected as controls and the 40 EBV-positive sera obtained from primary-infected patients and giving positive results with an ELISA test (EBNA-VCA-EA) for the detection of the IgMs and negative results with a Behring ELISA test for the detection of the anti-EBNA1 human IgGs.

The results obtained with the ELISA test using the reagent according to the invention VCAp18/SEQ ID No. 2+MIXO (P,G) for the detection of the IgG-A-Ms are presented in FIG. 11A and a detailed study of the isotype response of the different sera is illustrated in FIG. 11B.

Only six EBNA1-negative sera give a result above the cut-off as regards the reactivity with respect to the IgG-A-Ms (FIG. 11A).

All these sera belong to the group consisting of the IgG-negative sera (40%). Two of them do not react with any test and are considered as false-negatives.

Furthermore, they are the only two to be IgM-negative (FIG. 11B). Following this IgM-negativity, these two sera were tested in immunofluorescence (IF) for confirmation of their seropositivity. The titres obtained correspond to values at one-tenth and one-fortieth. These very low titres indicate great precociousness of the EBV infection. One explanation might be the detection of another antigen such as EA included in commercial kits or more probably a cross-reaction with another virus of the Herpes group (CMV, HSV and the like).

Moreover, the other 4 sera which are also IgG-negative have low IgM and IgA levels indicating an early phase of primary infection.

The specificity of the IgM reactivity was studied by neutralizing the IgG reactivity with precipitating agents.

As illustrated in FIGS. 12A and 12C, the untreated sera and the treated sera (RF-absorbent) do not exhibit any difference in reactivity.

On the other hand, the preadsorption of the IgGs induces two false-negative results (FIG. 12B). However, the latter two sera are IgG-A-M-positive. One of them proved only IgA-positive, whereas the other provides a high IgG response and a low IgA response.

FIG. 13 compares an ELISA test using a reagent according to the invention (VCAp18/SEQ ID No. 2+MIXO(P,G) for the detection of the IgGs and a Behring ELISA test for the specific detection of the anti-EBV IgMs, in which a nuclear extract of the cells infected with an EBV is used as antigen.

No correlation is observed between the values obtained with these two ELISA tests. A shift in the absorbance values is observed with the reagent according to the invention. A serum giving a result which is difficult to interpret with the Behring test is efficiently detected with the ELISAs, using a reagent according to the invention, for the specific detection of the anti-VCA IgMs and IgGs.

c) Relevance of the Reagent According to the Invention VCAp18/SEQ ID No. 2+MIXO(P,G) for the Differential Serodiagnosis of the Isotypes Produced During an EBV Infection Discrimination between a previous infection (healthy carrier) and a primary infection was up until now based on the IgM and IgG reactivity obtained with the Behring ELISA tests using a VCA+EBNA+EA reagent for the detection of the IgMs and IgGs.

Figures 15A, 15B:
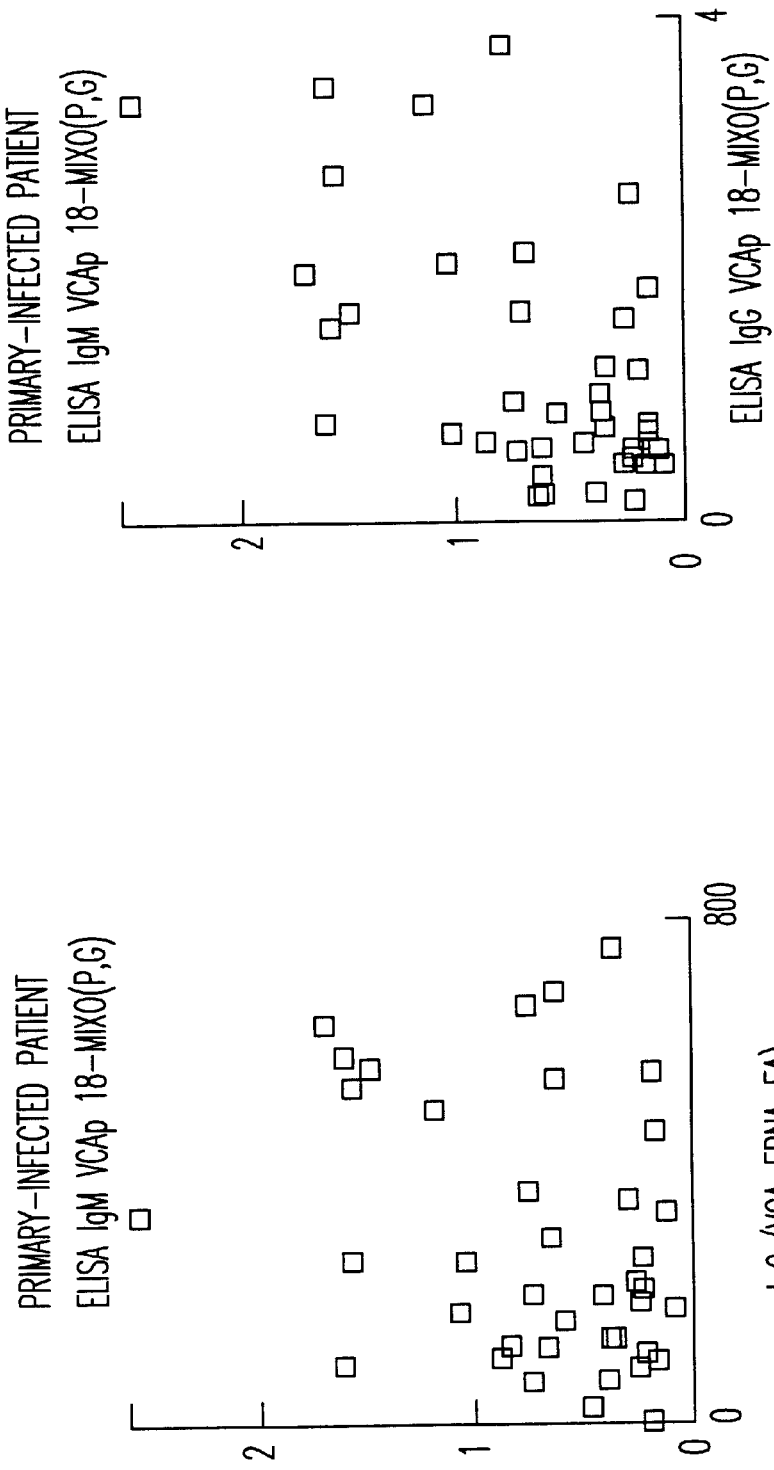
FIG. 15 illustrates the comparison of the absorbance value obtained for the detection of the IgGs in sera from primary-infected subjects, with a VCA-EBNA-EA Behring ELISA test or a VCAp18/SEQ ID No. 2+MIXO(P,G) ELISA test according to the invention with the IgM reactivity obtained with the aid of an ELISA test using a reagent according to the invention VCAp18/SEQ ID No. 2+MIXO(P,G).

FIGS. 14 and 15 illustrate the comparative results obtained with the reagent according to the invention VCAp18/SEQ ID No. 2+MIXO(P,G) for the detection of the human IgM response, in two EBV-positive populations studied with reference to their IgG level determined by the method according to the present invention and by conventional methods.

The absorbance values obtained with patients who have previously had an infection (healthy carriers) are distributed along the x-axis (FIG. 14A). This situation is in agreement with the results obtained in conventional serology with these type of patients (IgM-negative and IgG-positive, as determined with an immunofluorescence test).

Only one of these sera gave a strong IgM-positive signal with the reagent according to the invention VCAp18/SEQ ID No. 2+MIXO(P,G), indicating a primary infection (FIG. 14A); in addition, a strong IgG signal is obtained whereas by immunofluorescence only a weak IgG signal is observed.

This result confirms a reinfection (or a convalescence phase) since the IgA response is negative; this result shows the importance of the reagent according to the invention in the detection of the different isotypes.

A shift to the right, along the x-axis is in addition observed in the ELISA test carried out with the reagent according to the invention.

In the case of primary-infected patients, the values obtained with the ELISA tests are distributed along the y-axis.

In fact FIGS. 15(A and B) show a diagonal distribution.

The M and G isotypes appear sequentially, but almost simultaneously, after the onset of the infection.

Consequently, it is not surprising to detect the G isotype in the sera from primary-infected patients.

The relatively large subset of sera not situated along the diagonal or along the y-axis, but near the x-axis indicates a latent or persistent phase of the infection for these sera since most of them are IgA-positive. This situation appears less in FIG. 15B in which a reduction is observed in the number of sera, along the x-axis.

Surprisingly, the reagents according to the invention allow both the detection of the overall Ig reactivity (IgG-A-M) and the detection of the reactivity of each isotype (IgG, M or IgA).

The results described above are illustrated in Table III below.

TABLE III

| Antigen solid phase | Coating condition (μg/well) | Detection Ig isotype | Serum N | EBV + | Negative − | Specificity % | Serum | EBV N | Positive + | − | Sensitivity % |
|---|---|---|---|---|---|---|---|---|---|---|---|
| VCAp18/ SEQ ID No. 2 | 0.1 | Ig(G-A-M) | 28 | 0 | 28 | 100 | L | 46 | 42 | 4 | 91 |
| | | | | | | | P | 40 | 24 | 16 | 60 |
| | 1 | Ig(G-A-M) | 28 | 6 | 22 | 78 | L | 46 | 44 | 2 | 95 |
| | | | | | | | P | 40 | 34 | 6 | 85 |
| VCAp18/ SEQ ID No. 2 | 0.1 | IgM | 28 | 0 | 28 | 100 | L | 46 | nd | nd | |
| | | | | | | | P | 40 | 29 | 11 | 72 |
| | 1 | IgM | 28 | 0 | 28 | 100 | L | 46 | nd | nd | |
| | | | | | | | P | 40 | 38 | 2 | 95 |
| VCAp18/ SEQ ID No. 2 | 0.1 | IgA | 28 | 0 | 28 | 100 | L | 46 | nd | nd | |
| | | | | | | | P | 40 | 25 | 15 | 62 |
| | 1 | IgA | 28 | 0 | 28 | 100 | L | 46 | nd | nd | |
| | | | | | | | P | 40 | 29 | 11 | 72 |
| VCAp18/ SEQ ID No. 2 | 0.1 | IgG | 28 | 0 | 28 | 100 | L | 46 | nd | nd | |
| | | | | | | | P | 40 | 13 | 27 | 32 |
| | 1 | IgG | 28 | 1 | 27 | 96 | L | 46 | nd | nd | |
| | | | | | | | P | 40 | 24 | 16 | 60 |
| VCAp18/ SEQ ID No. 2 + MIXO (P,G) | 0.1 + 10 | Ig(G-A-M) | 28 | 0 | 28 | 100 | L | 46 | 46 | 0 | 100* |
| | | | | | | | P | 40 | 34 | 6 | 85 |
| | 1 + 10 | Ig(G-A-M) | 28 | 0 | 28 | 100 | L | 46 | nd | nd | |
| | | | | | | | P | 40 | 39 | 1 | 97* |
| | 0.1 + 10 | IgM | 28 | 0 | 28 | 100 | L | 46 | 42 | 4 | 91 |
| | | | | | | | P | 40 | 38 | 2 | 95 |
| | 1 + 10 | IgM | 28 | 0 | 28 | 100 | P | 40 | 38 | 2 | 95 |
| | 0.1 + 10 | IgA | 28 | 0 | 28 | 100 | L | 46 | 28 | 18 | 61 |
| | | | | | | | P | 40 | 30 | 10 | 75 |
| | 1 + 10 | IgA | 28 | 0 | 28 | 100 | P | 40 | 33 | 7 | 83 |
| | 0.1 + 10 | IgG | 28 | 0 | 28 | 100 | L | 46 | 44 | 2 | 96 |
| | | | | | | | P | 40 | 24 | 16 | 60 |

TABLE III-continued

| Antigen solid phase | Coating condition (μg/well) | Detection Ig isotype | Serum N | EBV + | Negative - | Specificity % | Serum | EBV N | Positive + | - | Sensitivity % |
|---|---|---|---|---|---|---|---|---|---|---|---|
| | 1 + 10 | IgG | 28 | 0 | 28 | 100 | L | 46 | nd | nd | |
| | | | | | | | P | 40 | 29 | 11 | 72 |

This table shows the results obtained for 86 sera from subjects who are healthy carriers or from primary-infected subjects when the peptide VCAp18/SEQ ID No. 2 is used alone; 60% and 51% of positive responses are observed for these two populations, respectively, without loss of specificity.

Legend to Table III: nd=not determined; L=sera from healthy carriers (IgM-negative and IgG-positive); P=sera from primary-infected patients (IgM-positive and IgG in most cases). There is no indication as regards the IgAs with the conventional ELISAs.

When a reagent according to the invention VCAp18/SEQ ID No. 2+MIXO(P,G) is used, the percentages of positive results obtained in the two populations reach 97% and 100%, respectively. The latter result (Table III, *) depends on the concentrations for use which are selected for the peptide VCAp18/SEQ ID No. 2 and relates to the overall IgG-A-M reactivity.

If all the results are observed, a good correlation (98.8%) is observed between the conventional methods and the method using a reagent according to the invention (good sensitivity).

This demonstrates the relevance of the IgG-A-M serodetection, which is usually considered not to be very sensitive and to be only IgG-specific.

In fact, with the reagents according to the present invention, when the individual IgG, IgA and IgM sensitivities are compared with the results obtained with the IgG-A-M detection according to the invention, the latter corresponds approximately to the sum of the results obtained for each isotype; in particular, none of the isotype-positive sera was negative, when an overall Ig(GAM) reactivity is detected according to the method according to the present invention.

These results show the specificity and the sensitivity of the reagent according to the invention.

In addition, these results show that the sera from subjects who have previously had an infection have residual levels of IgM.

The IgM reactivities are surprising because they are in contrast to the results obtained with the prior art tests.

These results suggest in particular that the IgMs persist with the IgGs for a long period after infection.

As evident from the above, the invention is not at all limited to its embodiments, implementations and applications which have just been described more explicitly; it embraces on the contrary all the variants which may occur to the specialist in this field, without departing from the framework or the scope of the present invention.

What is claimed is:

1. A reagent for diagnosing a viral infection, comprising (1) an immunodominant fragment of a protein of the virus comprising at most 60 amino acids; and (2) a mixture of convergent combinatory peptides obtained by systematic or partial replacement of each amino acid of the immunodominant fragment with another amino acid, according to a suitable replaceability matrix.

2. The reagent according to claim 1, wherein the viral infection is Epstein Barr viral infection and the reagent comprises (1) a C-terminal fragment of at most 60 amino acids of SEQ ID NO:1; and (2) a mixture of convergent combinatory peptides derived from the C-terminal fragment of SEQ ID NO:1.

3. The reagent according to claim 2, wherein the C-terminal fragment is selected from the group consisting of SEQ ID NO:2, SEQ ID NO:3, SEQ ID NO:4, and SEQ ID NO:5.

4. The reagent according to claim 2, wherein the combinatory peptides are obtained by systematic replacement of each amino acid of the C-terminal fragment with another amino acid.

5. The reagent according to claim 2, wherein the combinatory peptides are obtained by partial replacement of each amino acid of the C-terminal fragment with another amino acid.

6. The reagent according to claim 5, wherein the C-terminal fragment peptide is SEQ ID NO:2 and at least one of the proline residues, and the sequence Gly Ser Gly Gly Gly Gly (SEQ ID No.6) are conserved.

7. The reagent according to claim 5, wherein the C-terminal fragment peptide is SEQ ID NO:3, and at least one of the proline residues, the serine residues, and the alanine residues of the repetitive sequences are conserved.

8. The reagent according to claim 5, wherein the C-terminal fragment is SEQ ID NO:4, and at least one of the serine residues, the proline residues, the alanine residues, the sequence Gly Ser Gly Gly Gly Gly (SEQ ID No. 6), and the sequence Ala Ala Ala Ser Ala Ala Ala Ala (SEQ ID No. 7) of SEQ ID NO:4 are conserved.

9. The reagent according to claim 5, wherein the C-terminal fragment is SEQ ID NO:5, and at least one of the serine residues, the alanine residues, and the sequence Ala Ala Ala Ser Ala Ala Ala Ala (SEQ ID No. 7) of SEQ ID NO:5 are conserved.

10. The reagent according to claim 1, wherein the reagent is attached to a solid support.

11. The reagent according to claim 2, wherein the ratio of the C-terminal fragment of SEQ ID NO:1 to the mixture of convergent combinatory peptides if from 1:10 to 1:100.

12. Method for the diagnosis of a viral infection, by an immunoenzymatic method, characterized in that it uses a diagnostic reagent according claim 1.

13. Diagnostic method, characterized in that, for the diagnosis of an EBV infection by an immunoenzymatic method, it comprises:

bringing a serum to be analysed into contact with a reagent according to claim 2, the addition of anti-human Ig antibodies coupled to an enzyme, and the qualitative and/or quantitative revealing of the anti-VCA antibodies which may be present in the serum to be analysed by addition of the enzyme substrate.

14. Method according to claim 13, characterized in that it comprises:

the attachment of a reagent according to any one of claims 2 to 11 onto a support, such as a microtitre plate, the addition of the serum to be analysed, and the detection of the attachment of the anti-VCA antibodies present in the said serum by addition of anti-human Ig (G-A-M) antibodies coupled to an enzyme, and the qualitative and/or quantitative revealing in a spectrophotometer by addition of the enzyme substrate.

15. A kit or box for the diagnosis of a viral infection, which comprises at least one diagnostic reagent according to claim 1.

16. The reagent according to claim 1, wherein the immunodominant fragment of the viral protein comprises from 20 to 30 amino acids.

17. The reagent according to claim 2, wherein the immunodominant fragment of the viral protein comprises from 20 to 30 amino acids.

18. The reagent according to claim 10, wherein the solid support is a microtitre plate.

* * * * *

SEQUENCE LISTING

<160> NUMBER OF SEQ ID NOS: 7

<210> SEQ ID NO 1
<211> LENGTH: 176
<212> TYPE: PRT
<213> ORGANISM: Epstein-Barr virus

<400> SEQUENCE: 1

```
Met Ala Arg Arg Leu Pro Lys Pro Thr Leu Gln Gly Arg Leu Glu Ala
1               5                   10                  15

Asp Phe Pro Asp Ser Pro Leu Leu Pro Lys Phe Gln Glu Leu Asn Gln
            20                  25                  30

Asn Asn Leu Pro Asn Asp Val Phe Arg Glu Ala Gln Arg Ser Tyr Leu
        35                  40                  45

Val Phe Leu Thr Ser Gln Phe Cys Tyr Glu Glu Tyr Val Gln Arg Thr
    50                  55                  60

Phe Gly Val Pro Arg Arg Gln Arg Ala Ile Asp Lys Arg Gln Arg Ala
65                  70                  75                  80

Ser Val Ala Gly Ala Gly Ala His Ala His Leu Gly Gly Ser Ser Ala
                85                  90                  95

Thr Pro Val Gln Gln Ala Gln Ala Ala Ala Ser Ala Gly Thr Gly Ala
            100                 105                 110

Leu Ala Ser Ser Ala Pro Ser Thr Ala Val Ala Gln Ser Ala Thr Pro
```

```
              115                 120                 125
Ser Val Ser Ser Ser Ile Ser Ser Leu Arg Ala Ala Thr Ser Gly Ala
        130                 135                 140
Thr Ala Ala Ala Ser Ala Ala Ala Val Asp Thr Gly Ser Gly Gly
145                 150                 155                 160
Gly Gly Gln Pro His Asp Thr Ala Pro Arg Gly Ala Arg Lys Lys Gln
                165                 170                 175

<210> SEQ ID NO 2
<211> LENGTH: 71
<212> TYPE: PRT
<213> ORGANISM: Artificial Sequence
<220> FEATURE:
<223> OTHER INFORMATION: Synthetic Peptide
<221> NAME/KEY: MISC_FEATURE
<222> LOCATION: (1)..(1)
<223> OTHER INFORMATION: Xaa = unknown amino acid

<400> SEQUENCE: 2

Xaa Ala Leu Ala Val Ala Leu Ala Ser Pro Thr His Arg Gly Leu Tyr
1               5                   10                  15

Ser Glu Arg Gly Leu Tyr Gly Leu Tyr Gly Leu Tyr Gly Leu Tyr Gly
            20                  25                  30

Leu Asn Pro Arg His Ile Ser Ala Ser Pro Thr His Arg Ala Leu Ala
        35                  40                  45

Pro Arg Ala Arg Gly Gly Leu Tyr Ala Leu Ala Arg Gly Leu Tyr
    50                  55                  60

Ser Leu Tyr Ser Gly Leu Asn
65                  70

<210> SEQ ID NO 3
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 3

Ser Thr Ala Val Ala Gln Ser Ala Thr Pro Ser Val Ser Ser Ser Ile
1               5                   10                  15

Ser Ser Leu Arg Ala Ala Thr Ser Gly Ala Thr Ala Ala Ala
            20                  25                  30

<210> SEQ ID NO 4
<211> LENGTH: 58
<212> TYPE: PRT
<213> ORGANISM: Artificial Sequence
<220> FEATURE:
<223> OTHER INFORMATION: Synthetic Peptide

<400> SEQUENCE: 4

Ser Thr Ala Val Ala Gln Ser Ala Thr Pro Ser Val Ser Ser Ser Ile
1               5                   10                  15

Ser Ser Leu Arg Ala Ala Thr Ser Gly Ala Thr Ala Ala Ala Ser Ala
            20                  25                  30

Ala Ala Ala Val Asp Thr Gly Ser Gly Gly Gly Gly Gln Pro His Asp
        35                  40                  45

Thr Ala Pro Arg Gly Ala Arg Lys Lys Gln
    50                  55

<210> SEQ ID NO 5
```

-continued

```
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 5

Ser Val Ser Ser Ser Ile Ser Ser Leu Arg Ala Ala Thr Ser Gly Ala
1               5                   10                  15

Thr Ala Ala Ala Ser Ala Ala Ala Ala Val Asp Thr Gly Ser
            20                  25                  30

<210> SEQ ID NO 6
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 6

Gly Ser Gly Gly Gly Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 7

Ala Ala Ala Ser Ala Ala Ala Ala
1               5
```